(12) United States Patent
Brentano et al.

(10) Patent No.: US 6,218,107 B1
(45) Date of Patent: *Apr. 17, 2001

(54) COMPOSITIONS AND METHODS FOR DETECTING THE PRESENCE OF *MYCOBACTERIUM KANSASSII*

(75) Inventors: Steven T. Brentano, Santee; Irene Andruszkiewicz, San Diego; Caroline F. Knott, Solana Beach, all of CA (US)

(73) Assignee: Gen-Probe Incorporated, San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/856,963

(22) Filed: May 15, 1997

Related U.S. Application Data
(60) Provisional application No. 60/015,852, filed on May 22, 1996.

(51) Int. Cl.⁷ .............................. C07H 21/04; C07H 21/02

(52) U.S. Cl. ............................................ 435/6; 536/24.32

(58) Field of Search ......................... 435/6, 810; 536/24, 536/32

(56) References Cited

U.S. PATENT DOCUMENTS

| | | | |
|---|---|---|---|
| 4,683,195 | 7/1987 | Mullis et al. ............................ | 435/6 |
| 4,851,330 | 7/1989 | Kohne ..................................... | 435/6 |
| 5,030,557 | 7/1991 | Hogan et al. ............................ | 435/6 |
| 5,185,439 | 2/1993 | Arnold et al. ...................... | 536/24.3 |
| 5,283,174 | 2/1994 | Arnold et al. ........................... | 435/6 |
| 5,500,341 | 3/1996 | Spears .................................... | 435/6 |
| 5,614,390 | 3/1997 | McCaslin et al. ................. | 435/91.2 |
| 5,681,698 | * 10/1997 | Hogan et al. ............................ | 435/6 |

FOREIGN PATENT DOCUMENTS

| | | |
|---|---|---|
| 0313219 | 4/1989 | (EP) . |
| 0669402 | 8/1995 | (EP) . |
| 8803957 | 6/1988 | (WO) . |
| 8810315 | 12/1988 | (WO) . |
| 8901050 | 2/1989 | (WO) . |
| 0408295 | 1/1991 | (WO) . |
| 9322461 | 11/1993 | (WO) . |
| 9403472 | 2/1994 | (WO) . |

OTHER PUBLICATIONS

Endozo et al., "Identification of a Sub–group of *Mycobacterium kansasii* by rRNA Sequence Analysis," Abstracts of the 95th General Meeting of the American Society for Microbiology 133 at U–96 (May 21–25, 1995).

Yang et al., "Isolation of a DNA Probe for Identification of *Mycobacterium kansasii,* including the Genetic Subgroup," *Journal of Clinical Microbiology* 31(10):2769–2772 (1993).

Adams et al. (editors), "Ch. 2—The Structure of the nucleic acids," *The Biochemistry of the Nucleic Acids*, 11th edition, Chapman & Hall, New York, pp. 5–39 (1992)(1321).

Dattagupta et al., U.S. Patent Application No. 08/215,081 filed Mar. 16, 1994.

Lane et al., "Rapid determination of 16S ribosomal RNA sequences for phylogenetic analyses," *Proc. Natl. Acad. Sci. USA* 82:6955–6959 (1985).

Murakawa et al., "Direct Detection of HIV–1 RNA from AIDS and ARC Patient Samples," *DNA* 7:287–295 (1988).

Ross et al., "Identification of a Gentically Distinct Subspecies of *Mycobacterium kansasii*," *Clinical Microbiology* 30:2930–2933 (1992).

Sambrook et al., "Ch. 11—Synthetic Oligonucleotide Probes," in *Molecular Cloning: A Laboratory Manual, 2nd edition*, Cold Spring Harbor Laboratory Press, pp. 11.2–11.61 (1989).

Wayne and Kubica, "Section 16. The *Mycobacteria,* " in *Bergy's Manual of Systemic Bacteriology*, vol. 2, edited by Sneath et al., Williams and Wilkins, Baltimore, pp. 1435–1457 (1986).

* cited by examiner

*Primary Examiner*—Stephanie Zitomer
(74) *Attorney, Agent, or Firm*—Charles B. Cappellari

(57) ABSTRACT

The featured invention discloses and claims oligonucleotide hybridization assay probes and helper oligonucleotides which are designed to be complementary to specific regions of *M. kansasii* rRNA or the DNA encoding it, or to an oligonucleotide or nucleic acid comprising, consisting essentially of, or consisting of, a *M. kansasii* rRNA or rDNA nucleotide sequence.

The hybridization probes of the present invention are designed to hybridize to a target nucleic acid in a region of the molecule having a specific target nucleotide sequence under conditions which allow the selective detection of the target nucleic acid. The probes are further designed to detect *M. kansasii* typical as well as atypical strains.

The present invention also discloses and claims double-stranded nucleic acid hybrid molecules formed between the hybridization probes and their specific target nucleic acids.

69 Claims, 1 Drawing Sheet

FIGURE 1

| | |
|---|---|
| typical | GCCGC AGCGA AAGCG AGUCU GAAUA GGGCG UAUCG CGCGC |
| BOV | GCCGC AGCGA AAGCG AGUCU GAAUA GGGCG UAUCA CGCGU |
| COU | GCCGC AGCGA AAGCG AGUCU GAAUA GGGCG UAUCA CGUGC |
| | |
| typical | GAGCG UGUGU AGUGG CGUGU UCUGG ACCCG AAGCG G |
| BOV | GAGCG UGUGU AGUGG CGUGU UCUGG ACCCG AAGCG G |
| COU | AAGCG UGUGU AGUGG CGUGU UCUGG ACCCG AAGCG G |

COMPOSITIONS AND METHODS FOR DETECTING THE PRESENCE OF *MYCOBACTERIUM KANSASSII*

This application claims the benefit of U.S. Provisional application No. 60/015,852, filed May 22, 1996.

FIELD OF THE INVENTION

The invention described and claimed herein relates to the design and use of nucleic acid probes and helper oligonucleotides for detecting nucleic acids from the bacterial species *Mycobacterium kansasii* in test samples, e.g., from throat swabs, tissue samples, body fluids, and from cultures.

BACKGROUND OF THE INVENTION

*Mycobacterium kansasii* is a slowly growing photochromogenic bacterium that causes chronic pulmonary disease resembling tuberculosis (Wayne. L. G. and G. P. Kubica, 1986, "The Mycobacteria," pp. 1435–1457, in Sneath et al., eds., BERGEY'S MANUAL OF SYSTEMIC BACTERIOLOGY, Vol. 2, Williams and Wilkins, Baltimore). Among mycobacteria other than *M. tuberculosis* and *M. avium* complex strains, *M. kansasii* is one of the most frequently isolated species.

Disseminated infections caused by non-tuberculosis mycobacteria such as *M. kansasii* have become an increasing public health concern as the number of AIDS infected individuals increases. *M kansasii* is currently the second most common nontuberculosis mycobacterium causing disseminated disease in HIV-infected patients (after the *M. avium* complex).

Classical methods for identification of mycobacteria involve various biochemical techniques, acid fast staining, cell morphioligy and HPLC analysis. *M. kansasii* cells are moderately long to long rods. Colonies range from flat to raised and smooth to rough colony types. *M. kansasii* colonies are typically nonpigmented when grown in the dark and turn yellow following exposure to light (photochromogenic). Biochemical tests include positive nitrate reduction, tween and urea hydrolysis, catalase activity and niacin production. It can take several months to speciate a mycobacteria isolate using these identification methods.

Certain subspecies of M. kansasii are atypical. See for example Ross et al., J. Clin. Microbiol. 30:2930–2933 (1992). These atypical subspecies have variations in their 23S rRNA sequence, and therefore are not necessarily detectable with probes directed to 23S rRNA derived from the typical strains of *M. kansasii*. However, these atypical strains have been implicated as causative agents in infections, and it is therefore important to be able to identify the atypical strains as M. kansasii. Therefore, the term *M. kansasii* as used herein refers to both typical and atypical strains of the organism.

It is therefore an object of the present invention to provide nucleic acid hybridization probes for the rapid and specific detection of *M. kansasii* in test samples and particularly in human clinical specimens. Further, it is an object of the present invention to provide probes capable of detecting formerly undetectable subspecies of *M. kansasii*.

As used herein, the term "test sample" is intended to mean any sample suspected of containing the intended target nucleic acid, and includes but is not limited to: biological samples, body fluids or exudate such as urine, blood, milk, cerebrospinal fluid, sputum, saliva, stool, lung aspirates, throat or genital swabs, clinical specimens containing one or more of the foregoing, environmental samples, food samples and laboratory samples.

Nucleic acid hybridization is the process by which two nucleic acid strands having completely or partially complementary nucleotide sequences come together under predetermined reaction conditions to form a stable, double-stranded hybrid with specific hydrogen bonds. Either nucleic acid strand may be a deoxyribonucleic acid (DNA) or a ribonucleic acid (RNA); thus hybridization can involve RNA:RNA hybrids, DNA:DNA hybrids, or RNA:DNA hybrids.

Thus, as used in this application, the term "hybridization" refers to the ability of two completely or partly complementary single nucleic acid strands to come together in an antiparallel orientation to form a stable structure having a double-stranded region. The two constituent strands of this double-stranded structure, sometimes called a hybrid, are held together with hydrogen bonds. Although these hydrogen bonds most commonly form between nucleotides containing the bases adenine and thymine or uracil (A and T or U) or cytosine and guanine (C and G), base pairing can form between bases which are not members of these "canonical" pairs. Non-canonical base pairing is well-known in the art. See e.g., *The Biochemistry of the Nucleic Acids* (Adams et al., eds., 1992).

Nucleic acid hybridization is a common method for detecting and quantitating target nucleic acids having specific nucleotide sequences. Such methods are useful for identifying and classifying organisms, diagnosing infectious diseases and genetic abnormalities, testing food and drugs, and identifying criminal suspects, among numerous other goals. Typically, nucleic acid hybridization assays use a labeled oligonucleotide hybridization assay probe having a nucleic acid sequence complementary to the target sequence. Such labels are well known in the art, and may include radioactive isotopes, enzymes, or fluorescent, luminescent, or chemiluminescent groups; the Applicants prefer the use of chemiluminescent acridinium esters as labels. See Arnold et al. U.S. Pat. No. 5,185,439, which enjoys common ownership with the present application and is incorporated by reference herein. The probe is mixed with a sample suspected of containing a nucleic acid having the target sequence under hybridization conditions suitable for allowing annealing of the two strands by hydrogen bonding in the region of complementarity. The probe then hybridizes to the target nucleic acid present in the sample. The resulting hybrid duplex may be detected by various techniques well known in the art, such as hydroxyapatite adsorption. Also included among these techniques are those that involve selectively degrading the label present on unhybridized probe and then measuring the amount of label associated with the remaining hybridized probe, as disclosed in Arnold et al., U.S. Pat. No. 5,283,174, which enjoys common ownership with the present application and is incorporated by reference herein. This latter technique, called the hybridization protection assay (HPA), is presently preferred by the Applicants.

Often a test sample will not contain a great enough number of nucleic acid molecules to permit direct detection or quantification by nucleic acid hybridization due to the sensitivity limits of the particular label used. In such a case, the amount of detectable target nucleotide sequence is increased before nucleic acid hybridization is used to identify its presence or amount in the test sample. This procedure is termed nucleic acid amplification, and the method of increasing the amount of the target nucleic acid is referred to as amplifying the target nucleic acid or target nucleotide sequence.

Amplification methods involve the use of at least one nucleic acid strand containing a target nucleotide sequence as a template in a nucleic acid polymerizing reaction to produce a complementary second strand containing the target nucleotide sequence. Amplification can be performed on both the sense and anti-sense strands of a duplex nucleic acid molecule containing the target nucleotide sequence. By repeating this process, using the product nucleic acids as templates in subsequent cycles, the number of nucleic acid molecules having the target nucleotide sequence increases rapidly.

A number of amplification methods have been described; among these are various embodiments of the polymerase chain reaction (PCR), (see e.g., Mullis et al., U.S. Pat. No. 4,683,195), and methods which utilize in vitro transcription (RNA synthesis) in one or more step of the procedure, (see e.g., Murakawa et al., *DNA* 7:287–295, Burg et al. PCT Publication No. W089/1050, Gingeras et al., PCT Publication No. WO088/10315, Gingeras et al. European Patent No. EP0373960, McDonough, et al., PCT Publication No. WO 94/03472, Kacian, et al., PCT Publication No. WO 93/22461, and Dattagupta, et al. (filed in the United States Mar. 16, 1994, U.S. patent application Ser. No. 08/215,081). The disclosure of these references are incorporated by reference herein; the last two of these references enjoy common ownership with the present application.

A hybridization assay probe is used to detect, indicate and/or quantify the presence of the intended target nucleic acid; such a probe is usually labeled with a radioactive or luminescent atom or a detectable chemical group, such as a chemiluminescent moiety. Applicants prefer using acridinium ester derivatives as a labeling reagent. However, the presence of the intended target nucleic acid can also be detected without the use of a labeled probe. For example, hybrids formed between the probe and the target nucleic acid can be isolated using hydroxyapitite or gel filtration, or can be visualized by using non-denaturing gel electrophoresis. Sometimes the intended target nucleic acid will include any of a population of different nucleic acid molecules with nucleotide sequences usually derived from a biological source. By way of example only, and not of limitation, the target nucleotide sequence may be shared by the nucleic acids of a genus of organisms (but not by organisms outside the genus), the detection of any of which is desired. Alternatively, the target nucleotide sequence may be unique to a species of organism or to a strain of that species.

Not all probes are necessarily intended to be detectable. Some hybridization probes, termed "helper oligonucleotides" or "helper probes," are designed to facilitate the ability of a separate assay probe to bind to its target nucleotide sequence. Although not wishing to be bound by theory, Applicants believe helper probes facilitate binding of the assay probe by locally decreasing the amount of intramolecular hydrogen-bonding in the target nucleic acid, thus making the target nucleotide sequence more available for specific hybridization with the labeled probe. Depending on the location of the labeled probe's binding site and the secondary structure of the target nucleic acid, helper probes may be directed to nucleotide sequence regions proximal to the labeled probe's binding site, or directed to regions distal from the binding site which nevertheless affect probe binding. Helper probes are described in Hogan et al., U.S. Pat. No. 5,030,557 which enjoys common ownership with the current application, and which is incorporated by reference herein.

Descriptions of the use of nucleic acid hybridization to detect the presence of particular nucleic acid sequences are given in Kohne, U.S. Pat. No. 4,851,330 and in Hogan et al., International Patent Application No. PCT/US87/03009; both of these references enjoy common ownership with the present application, and are incorporated by reference herein. Hogan describes methods for determining the presence of a non-viral organism or a group of non-viral organisms in a sample (e.g., sputum, urine, blood and tissue sections, food, soil and water) using nucleic acid hybridization techniques.

Hogan, supra, also describes a number of hybridization probes which specifically detect only targeted ribosomal RNA (rRNA) nucleotide sequences belonging to a specific organism or group of organisms.

SUMMARY OF THE INVENTION

The featured invention discloses and claims oligonucleotide hybridization assay probes and helper oligonucleotides which are designed to be complementary to specific regions of *M. kansasii* rRNA or the DNA encoding it, or to an oligonucleotide or nucleic acid comprising, consisting essentially of, or consisting of, a M. kansasii rRNA or rDNA nucleotide sequence.

The hybridization probes of the present invention are designed to hybridize to a target nucleic acid in a region of the molecule having a specific target nucleotide sequence under conditions which allow the selective detection of the target nucleic acid.

Thus, a basic and novel characteristic of the hybridization probes and helper oligonucleotides of the present invention is their ability, under appropriate, defined hybridization reaction conditions, to preferentially hybridize to a predetermined region of a target *M. kansasii* nucleic acid over non-targeted nucleic acids or nucleic acid regions. This specificity is a function of the degree of complementarity between the nucleotide sequences of the regions of the target nucleic acid and hybridization probe involved in the hydrogen-bonded hybridization complex, as well as the hybridization reaction conditions.

The present invention also discloses and claims double-stranded nucleic acid hybrid molecules formed between the hybridization probes and their specific target nucleic acids. Hybrids formed between assay probes and target nucleic acid molecules are useful for the detection and/or quantification of *M. kansasii,* since these structures may be physically or chemically distinguished from unhybridized assay probe after the hybridization reaction. For example, hybrids formed between the assay probes and target nucleic acid molecules can be segregated from unhybridized assay probes through the use of hydroxyapitite, gel filtration, gel electrophoresis, and other related methodologies. When labeled assay probes are used, label present on the assay probes can be detected as part of the hybrids such that the label on the hybrids indicates the presence of the target nucleic acid in the original sample. When unlabeled assay probes are used, the presence of the hybrids can be detected through spectrophotometry, dye binding, and other well known methods.

Alternatively, the presence of hybrids can be detected when labeled assay probes are used without the necessity to physically segregate the hybrids from the unhybridized labeled probe. As disclosed in Arnold et al U.S. Pat. No. 5,283,174, previously incorporated by reference herein, is selective degradation of the label present on unhybridized probe. This latter technique, called the hybridization protection assay (HPA), is presently preferred by the Applicants.

Thus, it is an object of the present invention to provide oligonucleotide hybridization assay probes capable of distinguishing *M. kansasii* from other microorganisms in a test sample. These probes have a high degree of specificity for *M. kansasii* nucleic acids, and will hybridize thereto under hybridization conditions which do not favor hybridization of the same probe to nucleic acids from closely related organisms such as *M. gastri M. avium* and *M. intracellulare*. Thus, the use of hybridization assay probes allows the specific detection or quantification of *M. kansasii* in a test sample containing these organisms. These probes may be used alone in a hybridization assay, or may be used in conjunction with other assay probes and/or helper oligonucleotides. The hybridization assay probes may be used directly to detect unamplified target nucleic acids, or may be used to detect nucleic acids having *M. knsasii* nucleotide sequences obtained via nucleic acid amplification.

The probes of the invention can be either specific or non-specific for strains of *M. kansasii*. As noted above, atypical variants of *M. kansasii* exist which have different nucleic acid sequences in their 23S rRNA. Two such atypical subspecies, herein identified as the "BOV" and the "COU" subspecies, are identified below. Probes can be designed so as to be inclusive as to both typical and atypical subspecies of *M. kansasii*, or to be exclusive for one subspecies. Thus it is an object of the present invention to provide oligonucleotide hybridization assay probes and/or probe mixes capable of distinguishing all *M. kansasii* organisms (typical and atypical) from non-*M. kansasii* organisms. Further it is an object of the present invention to provide oligonucleotide hybridization assay probes which are capable of detecting and identifying one subspecies of *M. kansashi* organisms. Included in these probes are probes specific for the typical *M. kansasii* organisms, *M. kansasii* BOV subspecies, and *M. kansasii* COU subspecies.

It is another object of the present invention to provide methods for the detection of all *M. kansasii* organisms and to distinguish *M. kansasii* from non-*M. kansasii* organisms. Further, it is an object of the present invention to provide methods for distinguishing subspecies of *M. kansasii*, such as typical, BOV and COU, from each other.

It is another object of the present invention to allow for the rapid, specific, and reproducible identification of *M. kansasii* in a test sample derived from a throat swab or other sample by the use of hybridization assay probes and helper oligonucleotides directed to *M. kansasii* nucleic acids.

It is another object of the present invention to provide a composition to increase the hybridization rate of a *M. kansasii*-specific hybridization assay probe to its target nucleic acid, as well as to increase the stability of the hybrid thereby formed by using helper oligonucleotides capable of hybridizing to *M. kansasii* nucleic acids, thereby facilitating the binding of the labeled probe to its target.

BRIEF DESCRIPTION OF THE DRAWING

FIG. 1 shows the consensus sequences between nucleotides 622–680 (as it is numbered for the *E. coli* 23S rRNA; the "650 region") of 23S rRNA for typical *M. kansasii* (SEQ ID NO:1), as well as for two atypical variant strains referred to herein as "COU" (SEQ ID NO: 3) and "BOV" (SEQ ID NO:2).

DETAILED DESCRIPTION OF THE INVENTION

The present invention is directed to hybridization assay probes and helper oligonucleotides to be used for the specific detection of *M. kansasii* nucleic acids, including those from atypical strains of *M. kansasii*. All of the oligonucleotides disclosed and claimed herein share in common the fact that they contain at least one nucleotide sequence region complementary to that of a *M. kansasii* nucleic acid.

Definitions

The following terms have the indicated meanings in the specification unless expressly indicated otherwise.

By "target nucleic acid" is meant a single- or double-stranded nucleic acid having a target nucleotide sequence.

By "oligonucleotide" is meant a single-stranded nucleotide polymer of greater than 2 nucleotides in length, preferably between 10 and 100 nucleotides, most preferably between 12 and 50 nucleotides in length. Such oligonucleotides may be joined by phosphodiester linkages, by phosphorothioate linkages, or by other rare or non-naturally-occurring linkages. For example, an oligonucleotide can include peptide nucleic acids (PNAs). Furthermore, an oligonucleotide may have uncommon nucleotides or non-nucleotide moieties such as 2' methoxy or 2' halide ribopyranosyl moieties. An oligonucleotide as defined herein is a nucleic acid, preferably DNA, but may be RNA or have a combination of ribo- and deoxyribonucleotides covalently linked. Substitutions of rare or non-naturally occurring linkages and/or uncommon nucleotides or non-nucleotide moieties must not interfere with the ability of the oligonucleotide to hybridize with target sequences. Oligonucleotide probes of a defined sequence may be produced by techniques known to those of ordinary skill in the art, such as by chemical or biochemical synthesis, and by in vitro or in vivo expression from recombinant nucleic acid molecules, e.g., bacterial or retroviral vectors. As intended by this disclosure, an oligonucleotide does not consist of chromosomal DNA or the in vivo transcription products thereof.

By "target nucleic acid sequence," "target nucleotide sequence" or "target sequence" is meant a specific desired deoxyribonucleotide or ribonucleotide sequence comprising all or a part of the nucleotide sequence of a single-stranded target nucleic acid molecule, and the deoxyribonucleotide or ribonucleotide sequence perfectly complementary thereto.

A "substantially similar" nucleotide sequence is a nucleotide sequence identical to, or having no more than 20% mismatches, or internal deletions and/or additions (excluding RNA or DNA equivalent nucleotides) as compared to a particular identified nucleic acid sequence. An oligonucleotide having a substantially similar nucleotide sequence to an identified sequence in a reference nucleic acid shares the selective hybridization ability of that reference nucleic acid. In addition, an oligonucleotide having a substantially similar nucleotide sequence can form a stable, detectable hybrid with a nucleic acid having a perfectly complementary nucleotide sequence to the identified sequence under stringent hybridization conditions but will not form a stable detectable hybrid with a non-target nucleic acid sequence. These substantially similar sequences can have additional nucleotides at the 3' and/or 51 ends of the identified sequence.

"Stringent" hybridization assay conditions refer to conditions wherein a specific hybridization assay probe is able to hybridize with target nucleic acids (preferably rRNA or rDNA of *M. kansasii*) and not significantly with other nucleic acids present in the test sample derived either from other microorganisms (*M. gastri, M. avium* and *M. intracellulare*) or from humans. It will be appreciated that these conditions may vary depending upon factors including the GC content and length of the probe, the hybridization temperature, the composition of the hybridization reagent or solution, and the degree of hybridization specificity sought. Examples of specific stringent hybridization conditions are provided in the disclosure below.

By "probe" is meant a single-stranded oligonucleotide having a sequence partly or completely complementary to a nucleic acid sequence sought to be detected, so as to stably hybridize thereto under stringent hybridization conditions. In the case of a group or species-specific probe, the probe has the ability to stably hybridize to a target nucleic acid and not to non-target nucleic acids such as those from organisms outside the phylogenetic group or species under stringent hybridization conditions. Probes may, but need not, have regions which are not complementary to a target sequence, as long as such sequences do not substantially alter the probe's desired specificity under stringent hybridization conditions. If such non-complementary regions exist they may contain a 5' promoter sequence and/or a binding site for RNA transcription, a restriction endonuclease recognition site, a non-selective sequence permitting immobilization of the probe or hybridization with a specific second target nucleic acid, or may contain sequences which will confer a desired secondary or tertiary structure, such as a catalytic active site or a hairpin structure on the probe, on the target nucleic acid, or both. A probe may be labeled with a reporter group moiety such as a radioisotope, a fluorescent or chemiluminescent moiety, with an enzyme or other ligand, which can be used for detection or confirmation that the probe has hybridized to the target sequence. One use of a probe is as a hybridization assay probe; probes may also be used as in vivo or in vitro therapeutic oligonucleotides or antisense agents to block or inhibit gene transcription, mRNA splicing, or translation in diseased, infected, or pathogenic cells. -As used in this disclosure, the phrase "a probe (or oligonucleotide) having a nucleic acid sequence consisting essentially of a sequence selected from" a group of specific sequences means that the probe, as a basic and novel characteristic, will form a stable detectable hybrid with a nucleic acid in a nucleotide sequence region having a nucleotide sequence exactly complementary to one of the listed nucleic acid sequences of the group under stringent hybridization conditions. An exact complement under this definition includes the corresponding DNA or RNA sequence.

By "nucleic acid hybrid" or "hybrid" is meant a nucleic acid structure containing a double-stranded, hydrogen-bonded region, preferably of between 10 and 100 nucleotides in length, most preferably of between about 12 and 50 nucleotides in length, wherein each strand is complementary to the other and wherein the region is sufficiently stable under stringent hybridization conditions to be detected by means including but not limited to chemiluminescent or fluorescent light detection, autoradiography, or gel electrophoresis. Such hybrids may comprise RNA:RNA, RNA:DNA, or DNA:DNA duplex molecules.

By "complementary" is meant that the nucleotide sequences of similar regions of two single-stranded nucleic acids, or to different regions of the same single-stranded nucleic acid, have a nucleotide base composition that allows the single strands to hybridize together in a stable double-stranded hydrogen-bonded region under stringent hybridization conditions. When a contiguous sequence of nucleotides of one single stranded region is able to form a series of "canonical" hydrogen-bonded base pairs with an analogous sequence of nucleotides of the other single-stranded region such that A is paired with U or T, and C is paired with G, the nucleotides sequences are "perfectly" complementary.

By "conservatively modified variants" is meant nucleic acids or oligonucleotides having a nucleotide sequence that is complementary to a first nucleotide sequence region of a first nucleic acid, wherein the first nucleotide sequence region is perfectly complementary to a second nucleotide sequence region contained in a second "reference" nucleic acid. Conservatively modified variants have no more than 8 additional nucleotides at the and no more than 8 less nucleotides than the reference nucleic acid. It will be understood that such conservatively modified variants may have 5' and 3' non-complementary nucleotides which render the probe longer than the reference nucleotide sequence. Conservatively modified variants will form a stable detectable hybrid with a target nucleic acid region having a *M. kansasii* nucleotide sequence under stringent hybridization conditions, but will not form a stable detectable hybrid with non-target nucleic acid.

By "nucleic acid amplification" or "target amplification" is meant increasing the number of nucleic acid molecules having at least one target nucleic acid sequence.

By "helper oligonucleotide" is meant a normally unlabeled nucleic acid probe designed to hybridize with the target nucleic acid at a different locus than that of a labeled hybridization assay probe, thereby either increasing the rate of hybridization of the labeled probe, increasing the melting temperature($T_m$) of the target:labeled probe hybrid, or both.

Hybridization Conditions and Probe/Primer Design

Hybridization reaction conditions, most importantly the temperature of hybridization and the concentration of salt in the hybridization solution, can be selected to allow the hybridization probes of the present invention to preferentially hybridize to nucleic acids having a target *M. kansasii* nucleotide sequence over other, untargeted nucleic acids suspected of being present in the test sample. At decreased salt concentrations and/or increased temperatures (called increased stringency) the extent of nucleic acid hybridization decreases as hydrogen bonding between paired nucleotide bases in the double-stranded hybrid molecule is disrupted; this process is called "melting."

Generally speaking, the most stable hybrids are those having the largest number of contiguous perfectly matched (i.e., hydrogen-bonded) nucleotide base pairs. Thus, such hybrids would usually be expected to be the last to melt as the stringency of the hybridization conditions increases. However, a double-stranded nucleic acid region containing one or more mismatched, "non-canonical," or imperfect base pair (resulting in weaker or non-existent base pairing at that position in the nucleotide sequence of a nucleic acid) may still be sufficiently stable under conditions of relatively high stringency to allow the nucleic acid hybrid to be detected in a hybridization assay without cross reacting with other, non-targeted nucleic acids present in the test sample.

Hence, depending both upon the degree of sequence variation between nucleic acids of the target organism and those of non-target but closely-related organisms on one hand, and the degree of complementarity between the nucleotide sequence of a particular hybridization probe and that of the target nucleic acid on the other, one or more mismatches between the probe and the target will not necessarily defeat the ability of the oligonucleotide to hybridize to target over non-target nucleic acids.

The hybridization assay probes of the present invention were chosen, selected, and/or designed to maximize the difference between the melting temperatures of the probe:target hybrid ($T_m$, defined as the temperature at which half of the potentially double-stranded molecules in a given reaction mixture are in a single-stranded, denatured state)

and the $T_m$ of a mismatched hybrid formed between the probe and the rRNA or rDNA of the phylogenetically most closely-related organisms expected to be present in the test sample, but not sought to be detected. While the unlabeled amplification oligonucleotides and helper oligonucleotides need not have such an extremely high degree of specificity as the labeled hybridization assay probe to be useful in the present invention, they are generally designed in a similar manner to preferentially hybridize to target nucleic acids of one or more organism over other nucleic acids.

Nucleic Acid Sequences

Nucleotide sequences of the rRNA of *M. kansasii* and closely related organisms such as *M. gastri, M. avium* and *M. intracellulare* were obtained from published sources, or were independently determined by the Applicants using nucleic acid sequencing techniques well known in the art. See e.g., Lane et al. Proc. Natl. Acad. Sci. 82:6955 (1985).

By aligning the rRNA sequences of these various organisms, Applicants have discovered specific discrete regions of relative interspecies variability. Those regions which displayed the greatest amount of nucleotide sequence variability between the target organism, *M. kansasii,* and the "untargeted" organisms, eg *M. gastri, M. avium* and *M. intracellulare,* were chosen as potential target regions for the design of species-specific hybridization assay probes.

FIG. 1 shows the consensus sequences between nucleotides 622 and 680 (as it is numbered for the *E. coli* 23S rRNA; the "650 region") of 23S rRNA for typical *M. kansasii* as well as for two atypical variants strains herein labelled "COU" and "BOV." SEQ ID NO: 1 is from the typical strain, while SEQ ID NO: 2 is from strain BOV and SEQ ID NO: 3 is from strain COU.

Merely identifying putatively unique potential target nucleotide sequences does not guarantee that a functionally species-specific hybridization assay probe may be made to hybridize to *M. kansasii* rRNA or rDNA comprising that sequence. Various other factors will determine the suitability of a nucleic acid locus as a target site for species-specific probes. By way of example: increasing the GC content of the potential target nucleotide sequence (and thus of the double-stranded probe:target hybrid) generally increases the stability and thus the $T_m$ of the hybrid. The number of contiguous nucleotides within that sequence region which are identical to one or more of the "untargeted" organisms also affect the stability, and thus the $T_m$, of a partially mismatched hybrid between a probe perfectly complementary to *M. kansasii* rRNA, and a nucleic acid having rRNA nucleotide sequences of the untargeted organism or organisms. Thus, if the difference in the melting temperatures of the two hybrids is not sufficiently large, normally at least 2°–5° C., a probe may not be species specific despite being targeted to a unique region.

The desired temperature of hybridization and the hybridization solution composition (such as salt concentration) are two conditions having a major effect on the stability of double-stranded hybrids; these conditions must be taken into account in constructing a group- or species-specific probe. The thermal stability of hybrid nucleic acids increases with the ionic strength of the reaction mixture. On the other hand, chemical reagents which disrupt hydrogen bonds, such as formamide, urea, dimethyl sulfoxide and alcohols, can greatly reduce the thermal stability of the hybrids.

To maximize the specificity of a probe for its target, the subject probes of the present invention were designed to hybridize with their targets under conditions of high stringency. Under such conditions only single nucleic acid strands having a high degree of complementarity will hybridize to each other; single nucleic acid strands without such a high degree of complementarity will tend not to form hybrids. Accordingly, the stringency of the assay conditions (i.e., the temperature and the ionic strength) can determine the amount of complementarity which should exist between two nucleic acid strands in order to form a hybrid. In conjunction with the present invention, stringency is chosen to maximize the difference in stability between the hybrid formed between the probe and the target nucleic acid and potential hybrids formed between the probe and any single stranded non-target nucleic acids present.

Proper probe specificity may be designed by minimizing of the length of the probe having a nucleotide sequence perfectly complementary to sequences of non-target organisms, by avoiding G and C rich regions of homology to non-target sequences, and by constructing the probe to contain as many destabilizing mismatches to nontarget sequences as possible.

The length of the target nucleic acid sequence, and accordingly the total length of the probe sequence, can also be important to specificity. In some cases, there may be several nucleotide sequences in a particular "variable" region, differing in location and length, which may be used as species-specific probe targets. In some cases a species-specific probe cannot be designed to a particular rRNA variable region, either because the sequence region is not accessable to the probe, or for other reasons. While it is possible for nucleic acids that are not perfectly complementary to hybridize, the longest stretch of perfectly homologous base sequence will generally determine hybrid stability. Oligonucleotide probes of different lengths and base composition may be used.

Target regions which form strong intramolecular structures inhibitory to hybridization are less preferred target regions. Likewise, probe designs which result in extensive self-complementarity should be avoided. As explained above, hybridization is the association of two single strands of complementary nucleic acids to form a hydrogen-bonded double-stranded hybrid. Thus, if one or both of the two strands is wholly or partially involved in intramolecular or intermolecular bonding it will be less able to participate in the formation of a new intermolecular probe:target hybrid. Ribosomal RNA molecules, for example, are known to form very stable intramolecular helices and secondary structures by hydrogen bonding. By designing a hybridization assay so that a substantial portion of the targeted sequence remains in a single-stranded state until hybridization with the probe, the rate and extent of hybridization between probe and target may be greatly increased. One way this may be accomplished is by choosing as a target nucleotide sequence a sequence that is relatively uninvolved in intramolecular hydrogen-bonding. Alternatively or additionally, the hybridization assay probe may be used in a probe mix with helper oligonucleotides which can make the target site more accessible for hybridization with the hybridization assay probe. Such helper probes are generally described.

A number of formulae are available which provide an estimate of the melting temperature for perfectly matched oligonucleotides to their target nucleic acids. One such formula, $$T_m = 81.5 + 16.6(log_{10}[Na^+]) + 0.41(fraction\ G+C) - (600/N)$$

(where N=the length of the oligonucleotide in number of nucleotides) provides a good estimate for the $T_m$ for oligonucleotides between about 14 and 70 nucleotides in length. From such calculations, subsequent empirical verification or "fine tuning" of the $T_m$ may be made using screening techniques. (For further information on hybridization and oligonucleotide probes see e.g., Sambrook et al., *Molecular Cloning: A Laboratory Manual* (Cold Spring Harbor Laboratory Press 1989) hereby incorporated by reference herein (at Chapter 11). This reference, also provides estimates of the effect of mismatches on the $T_m$ of a hybrid.

Preparation of Oligonucleotides

An oligonucleotide is made of nucleotide subunits covalently joined together. The sugar groups of the nucleotide subunits may be ribose, deoxyribose, or modified derivatives thereof such as O-methyl ribose or 2' halide ribose. The nucleotide subunits may by joined by linkages such as phosphodiester linkages, modified linkages, or by non-nucleotide moieties that do not prevent hybridization of the oligonucleotide. Modified linkages include those linkages in which a standard phosphodiester linkage is replaced with a different linkage, such as a phosphorothioate linkage, or methylphosphonate linkage. As mentioned above, when used as a hybridization assay probe the oligonucleotide preferably contains a reporter group such as acridinium ester or a radioisotope to help identify hybridization of the probe to its target sequence.

All the oligonucleotides of the present invention, whether hybridization assay probes or helper oligonucleotides, may be modified with chemical groups to enhance their performance or to facilitate the characterization of amplification products. For example, backbone-modified oligonucleotides such as those having phosphorothioate or methylphosphonate groups which render the oligonucleotides resistant to the nucleolytic activity of certain polymerases allow the use of such enzymes in an amplification or other reaction. Another example of modification involves using non-nucleotide linkers (e.g., Arnold, et al., European Patent Application 88308766-0, hereby incorporated by reference herein) incorporated between nucleotides or at an end of the oligonucleotide chain which do not prevent hybridization or the elongation of the primer.

As disclosed above, the 5' end of the oligonucleotides may be modified to be resistant to the 5' -exonuclease activity present in some nucleic acid polymerases. Such modifications can be carried out by adding a non-nucleotide group to the terminal 5' nucleotide of the primer using techniques such as those described by Arnold, et al., supra entitled "Non-Nucleotide Linking Reagents for Nucleotide Probes," previously incorporated by reference herein.

Oligonucleotide Hybridization Assay Probes to *M. kansasii* rRNA and rDNA

The oligonucleotide hybridization assay probes disclosed and claimed herein are able to preferentially hybridize to target nucleic acids containing *M. kansasii* rRNA or rDNA nucleotide sequences over the nucleic acids of phylogenetically closely related bacterial species, preferably *M. gastri*, *M. avium* and *M. intracellulare*. These hybridization assay probes were designed, selected and/or chosen based upon a comparision of the nucleotide sequences of corresponding regions of the ribosomal RNA of *M. kansasii*, including the rRNA of *M. kansasii* variants, and said phlogenetically closely-related species.

The hybridization assay probes of the present invention are complementary to the following target rRNA nucleotide sequences:
SEQ ID NO: 4 GCGUAUCGCGCGCGAGCG,
SEQ ID NO: 5 GGCGUAUCACGCGUGAGCG,
SEQ ID NO: 6 GGCGUAUCACGUGCAAGCG,
and DNA versions thereof, having thymine substituted for uracil:

SEQ ID NO: 16 GCGTATCGCGCGCGAGCG,
SEQ ID NO: 17 GGCGTATCACGCGTGAGCG,
SEQ ID NO: 18 GGCGTATCACGTGCAAGCG,
or the nucleotide sequences perfectly complementary to these sequences.

The hybridization probes can vary in length from 10, 11, 12, 13, 14 or 15 to 100 nucleotides, and are preferably between 10 and 50 nucleotides in length. The probes must be capable of hybridizing to the identified target regions under stringent hybridization conditions, as defined above. As such, they must be at least 75% complementary to a contiguous region of at least 10 nucleotides of one of the target regions. Preferably the complementarity is at least 80%, and probes of 85%, 90%, 95% or more are most preferred, while probes with complementarity anywhere within the range of 75% to complete homology are hereby useful. The contiguous region can be greater than 10 nucleotides, for example 11, 12, 13, 14 or 15 nucleotides or more. Further, hybridization to the contiguous region must create a detectable hybrid with *M. kansasii* nucleic acid and must not be capable of forming a detectable hybrid with non-target nucleic acid such as that of *M. avium, M. gastri* or *M. intracellulare*.

Preferred embodiments of these oligonucleotide hybridization assay probes have the nucleotide sequence:
SEQ ID NO: 7 CGCTCGCGCGCGATACGC,
SEQ ID NO: 8 CGCTCACGCGTGATACGCC,
SEQ ID NO: 9 CGCTTGCACGTGATACGC,
SEQ ID NO: 10 CGCTTGCACGTGATACGCC,
and RNA versions thereof, having uracil substituted for thymine:
SEQ ID NO: 19 CGCUCGCGCGCGAUACGC,
SEQ ID NO: 20 CGCUCACGCGUGAUACGCC,
SEQ ID NO: 21 CGCUUGCACGUGAUACGC, and
SEQ ID NO: 22 CGCUUGCACGUGAUACGCC
or the nucleotide sequences perfectly complementary thereto.

Core sequences of these preferred oligonucleotide hybridization assay probes have the nucleotide sequence:
SEQ ID NO: 28 GCGCGCG
SEQ ID NO: 29 ACGCGUG
SEQ ID NO: 30 ACGUGCG
SEQ ID NO: 31 CGCGCGC
SEQ ID NO: 32 CACGCGU
SEQ ID NO: 33 CGCACGU The oligonucleotide hybridization probes can be used either singly or in combination. Probes corresponding to SEQ ID NO: 7 and their related probes can be used for the detection of typical *M. kansasii*; probes corresponding to SEQ ID NO: 8 and their related probes can be used for the detection of atypical *M. kansasli* BOV strains; probes corresponding to SEQ ID NO: 9 and SEQ ID NO: 10 and their related probes can be used for the detection of atypical *M. kansasii* COU strains. Combinations of these probes can be used for the detection of the corresponding combinations of *M. kansasii* strains.

The oligonucleotide hybridization assay probes of the present invention are preferably labeled with a detectable label such as a radioisotope, a fluorescent or chemiluminescent moiety, with an enzyme or other ligand, which can be used for detection or confirmation that the probe has hybridized to the target sequence. The Applicants prefer the use of chemiluminescent acridinium esters as labels. See Arnold et al., U.S. Pat. No. 5,185,439, which enjoys common ownership with the present application and is incorporated by reference herein. The assay probe is mixed with a sample suspected of containing a nucleic acid having the target sequence under hybridization conditions suitable for allowing annealing of the two strands by hydrogen bonding in the region of complementarity.

The probe or probes may also be combined with one or more unlabeled helper oligonucleotide to facilitate binding to the nucleic acid having the target *M. kansasii* nucleotide sequence. The probes then hybridize to the target nucleic acid present in the sample; the resulting hybrid duplexes may be separated and detected by various techniques well known in the art, such as hydroxyapatite adsorption and radioactive monitoring. Also included among these techniques are those that involve selectively degrading the label present on unhybridized probe and then measuring the amount of label associated with the remaining hybridized probe, as disclosed in Arnold et al. U.S. Pat. No. 5,283,174, which enjoys common ownership with the present application and is incorporated by reference herein. This latter technique, is presently preferred by the Applicants.

Helper Oligonucleotides used in the Detection of *M. kansashi*

Specific helper oligonucleotides were used to facilitate the hybridization of the hybridization assay probes to the target nucleic acid. Helper oligonucleotides are described in Hogan and Milliman, U.S. Pat. No. 5,030,557, which enjoys common ownership with the present application and is hereby incorporated by reference herein. Specific helper oligonucleotides for facilitating the specific detection of *M. kansasii* have nucleotide sequences complementary to a *M. kansasii* RNA nucleotide sequence of:

SEQ ID NO: 11 GCCGCAGCGAAAGCGAGUCUGAAUAGG,
SEQ ID NO: 12 UGUGUAGUGGCGUGUUCUGGACCCGAAGCGG,
and DNA versions thereof, having thymine substituted for uracil:
SEQ ID NO: 23 GCCGCAGCGAAAGCGAGTCTGAATAGG,
SEQ ID NO: 24 TGTGTAGTGGCGTGTTCTGGACCCGAAGCGG,
or the nucleotide sequences perfectly complementary thereto.

Preferred embodiments of these helper oligonucleotides are oligonucleotides having the nucleotide sequence of:
SEQ ID NO: 13 CGTATTCAGACTCGCTITCGCTGCGGC,
SEQ ID NO: 14 CCGCTTCGGGTCCAGAACACGCCACTACACA,
SEQ ID NO: 15 CTATTCAGACTCGCTmTCGCTGCGGC,
and RNA versions thereof, having uracil substituted for thymine,
SEQ ID NO: 25 CGUAUUCAGACUCGCUUUCGCUGCGGC,
SEQ ID NO: 26 CCGCUUCGGGUCCAGAACACGCCACUACACA,
SEQ ID NO: 27 CUAUUCAGACUCGCUUUCGCUGCGGC
or the nucleotide sequences perfectly complementary thereto.

Helper oligonucleotides generally may be used under stringent hybridization conditions, but are not necessarily species specific in their selectivity; i.e., the target nucleotide sequences for the helper oligonucleotides are not necessarily unique to the species *M. kansasii*. Preferably, hybridization assay probes are used in combination with helper oligonucleotides for the detection of *M. kansasii*.

The following examples of various embodiments of the present invention are for illustration only, and are not intended to limit the scope of the invention.

EXAMPLE 1

The DNA sequences coding for the 23S rRNA of various strains of *M. kansasii* were obtained using PCR amplification and cycle sequencing.

The various *M. kansasii* 23S rRNA sequences were compared to that of some of its closest phlyogentic neighbors, including *M. gastri*, *M. avium* and *M. intracellulare*. The region corresponding to an *E. coli* region near nucleotide 650 was found to have species specific variations which could be used for probe design. Probe SEQ ID NO: 7, probe SEQ ID NO: 8 and probe SEQ ID NO: 9 were chosen as providing the best distinction between the rRNA sequences of *M. kansasii*, including the atypical variants, and the other, closely related organisms.

EXAMPLE 2

In this experiment the specificity of the hybridization probe of nucleotide sequence of SEQ ID NO: 8 was tested through hybridization to closely related organisms *M. gastri* and *M. tuberculosis*. A helper oligonucleotide with the sequence of SEQ ID NO: 13 was used to facilitate the hybridization of the hybridization assay probes to the target nucleic acid. ATCC type strains of *M. kansasii; M. gastri* and *M. tuberculosis* were used. Organisms were inoculated into appropriate solid media and grown to log phase. A 1 µl loopful of growth from each culture was added to a bacterial lysing tube containing glass beads and 200 µl of lysing solution made of 5% sorbitol, 2.85 mM Sodium Azide, 3.7mM Hepes, 0.035% Triton X-100, 50mM succinate, 10mM EDTA, 10mM EGTA, 1% lithium lauryl sulphate (LLS), and 600mM LiCl. The tubes were sonicated 15 minutes at room temperature to lyse the organisms, and then inactivated for 10 minutes at 95° C.±5° C.

Probes were labeled with acridinium ester. For each probe, approximately $2.5 \times 10^6$ RLU (Relative Light Units - - - a measure of the number of photons detected by a luminometer) were used. Hybridizations were performed in a solution containing 0.05 M lithium succinate pH 5, 0.6 M LiCl, 1% (w/v) lithium lauryl sulfate (LLS), 10 mM ethylene diamine tetraacetic acid (EDTA), 10 mM ethylene glycol bis (beta-amino ethyl ether) N,N,N',N' tetraacetic acid (EGTA) at 60° C. for 15 minutes. Three hundred microliters of a solution containing 0.15 M sodium tetraborate pH 8.5, 1% TRITON® X-100 were added to each tube, and each reaction was incubated at 60° C. for 8 minutes, and cooled to room temperature. Detection of hybridization was analyzed in a Gen-Probe LEADER® I luminometer (Gen-Probe Incorporated, San Diego, Calif.). The luminometer automatically injects two reagents, the first comprising 1 mM nitric acid and 0.1% hydrogen peroxide and the second comprising 1 N sodium hydroxide. Assay results were given in RLU. RLU values greater than 30,000 RLU were considered a positive reaction. For these experiments, each reaction was performed in duplicate and the results are reported below.

TABLE 1

Detection of *M. kansasii* nucleic acid using hybridization assay probe having a nucleotide sequence of SEQ ID NO:8

|  | M. kansasii 533 | M. gastri 529 | M. gastri Cl 979 | M. gastri Cl 980 | M. gastri Cl 981 | M. tuberculosis 546A |
|---|---|---|---|---|---|---|
| repetition 1 | 821,729 | 6,157 | 4,427 | 5,770 | 6,826 | 3,810 |
| repetition 2 | 875,094 | 6,283 | 4,613 | 5,998 | 6,823 | 3,754 |
| mean | 848,412 | 6,220 | 4,520 | 5,884 | 6,825 | 3,782 |

EXAMPLE 3

In this experiment the the specificity of the hybridization probes of the nucleotide sequences of SEQ ID NO: 8 and SEQ ID NO: 9 was tested through hybridization of these probes to atypical strains of *M. kansasii*. Strains 1–9 were classified as the BOV strain, while strains 10–11 were classified as the COU strain. Cell growth and lysis, hybridization and detection were as described in Example 2. Hybridization was enhanced by the use of helper probes in each hybridization reaction. For probes of the nucleotide sequences of SEQ ID NO: 8, helper probes with the nucleotide sequence of SEQ ID NO: 14 and SEQ ID NO: 15 were used; for probes of the nucleotide sequences of SEQ ID NO: 9, helper probes with the nucleotide sequence of SEQ ID NO: 14 and SEQ ID NO: 13 were used. The results demonstrate the specificity of the probes for the two types of variant strains of *M. kansasii*.

TABLE 2

Detection of atypical *M. kansasii* nucleic acid using hybridization assay probes having a nucleotide sequence of SEQ ID NO:8 or SEQ ID NO:9.

| Organism | Strain Number | RLU from hybridization with SEQ ID NO:8 | RLU from hybridization with SEQ ID NO:9 |
|---|---|---|---|
| M. kansasii | 1 | 294,999 | 2,267 |
| M. kansasii | 2 | 462,898 | 1,751 |
| M. kansasii | 3 | 450,743 | 1,591 |
| M. kansasii | 4 | 467,158 | 1,082 |
| M. kansasii | 5 | 424,864 | 2,556 |
| M. kansasii | 6 | 456,904 | 1,693 |
| M. kansasii | 7 | 444,551 | 1,567 |
| M. kansasii | 8 | 382,435 | 2,593 |
| M. kansasii | 9 | 458,054 | 2,718 |
| M. kansasii | 10 | 1,686 | 765,969 |
| M. kansasii | 11 | 1,263 | 1,076,440 |

EXAMPLE 4

In this experiment the specificity of the hybridization probe having nucleotide sequence SEQ ID NO: 7 is demonstrated by hybridization with a number of different closely related organisms. Cell growth and lysis were as described in Example 2, using RNA released from one colony or >$10^8$ organisms. Hybridization was as described in Example 2, using helper probes with the nucleotide sequence of SEQ ID NO: 13 and SEQ ID NO: 14. Detection was as described in Example 2.

TABLE 3

Detection of *M. kansasii* nucleic acid using hybridization assay probes having a nucleotide sequence of SEQ ID NO: 7.

| ORGANISM | ATCC # | RLU Value |
|---|---|---|
| Mycobacterium avium | 25291 | 3,208 |
| M. bovis | 19210 | 2,739 |
| M. bovis BCG | 35734 | 3,522 |
| M. chelonae | 14472 | 2,576 |
| M. fortuitum | 6841 | 4,019 |
| M. gastri | 15754 | 3,015 |
| M. gordonae | 14470 | 1,885 |
| M. haemophilum | 29548 | 3,165 |
| M. intracellulare | 13950 | 1,373 |
| M. kansasii | 12478 | 123,797 |
| M. kansasii | 25414 | 201,751 |
| M. kansasii | 25101 | 206,062 |
| M. scrofulaceum | 19981 | 2,030 |
| M. simiae | 25275 | 1,764 |
| M. smegmatis | 14468 | 2,378 |
| M. tuberculosis (avir) | 25177 | 3,061 |
| M. tuberculosis (vir) | 27294 | 2,680 |
| M. ulcerans | 19423 | 1,905 |
| M. vaccae | 15483 | 1,905 |
| Nocardia asteroides | 19247 | 3,468 |

EXAMPLE 5

In this experiment the specificity of the hybridization probe having nucleotide sequence SEQ ID NO: 7 is further demonstrated by hybridization to a wide phylogenetic cross section of organisms. Cell growth and lysis was as described in Example 4. Hybridization and detection were as described in Example 4, using the same helper probes.

TABLE 4

Detection of *M. kansasii* nucleic acid using hybridization assay probes having a nucleotide sequence of SEQ ID NO: 7.

| ORGANISM | ATCC # | RLU Value |
|---|---|---|
| Acinetobacter calcoaceticus | 33604 | 5,327 |
| Bacillus subtilis | 6051 | 6,792 |
| Bacteroides fragilis | 23745 | 1,908 |
| Branhamella catarrhalis | 25238 | 2,730 |
| Campylobacter jejune | 33560 | 4,618 |
| Candida albicans | 18804 | 3,188 |
| Chromobacterium ciolaceum | 29094 | 9,401 |
| Clostridium perfringens | 13124 | 3,684 |
| Deinococcus radiodurans | 35073 | 3,556 |
| Derxia gummosa | 15994 | 2,033 |
| Pseudomonas aeruginosa | 25330 | 4,602 |
| Rahnella aquatilis | 33071 | 2,534 |
| Rhodospirillum rubrum | 11170 | 3,320 |
| Staphylococcus aureus | 12598 | 3,120 |
| Staphylococcus epidermidis | 12228 | 3,106 |

TABLE 4-continued

Detection of *M. kansasii* nucleic acid using hybridization assay probes having a nucleotide sequence of SEQ ID NO: 7.

| ORGANISM | ATCC # | RLU Value |
| --- | --- | --- |
| *Streptococcus mitis* | 9811 | 2,410 |
| *Streptococcus pneumoniae* | 6306 | 2,074 |
| *Vibrio parahaemolyticus* | 17802 | 8,516 |
| *Yersinia enterocolitica* | 9610 | 4,105 |

EXAMPLE 6

In this experiment the specificity of a probe mix containing all three designed probes (SEQ ID NO: 7, SEQ ID NO: 8 and SEQ ID NO: 9) and both helper probes (SEQ ID NO: 13 and SEQ ID NO: 14) was tested against standard strains of bacteria. A total of 55 ATCC (American Type Culture Collection) reference strains of mycobacteria were evaluated. These strains represented the most closely related organisms to *M. kansasii*. Standard specificity testing was performed using growth obtained from actively growing cultures of the ATCC strains, except for *Mycobacterium haemophilum*, for which cells were not available. Instead, *Mycobacterium haemophilum* rRNA was used at a concentration equivalent to that available from the growing cell cultures. Cell growth and lysis were as described in Example 2. Hybridization and detection were also as described in Example 2. All closely related mycobacteria produced negative results well below the 30,000 RLU cut-off.

TABLE 5

Specificity of probes having nucleotide sequences SEQ ID NO: 7, SEQ ID NO: 8 and SEQ ID NO: 9 for *M. kansasii* over other mycobacteria.

| ORGANISM | ATCC # | RLU |
| --- | --- | --- |
| *Mycobacterium acapulcensis* | 14473 | 1,821 |
| *Mycobacterium agri* | 27406 | 1,629 |
| *Mycobacterium aichiense* | 27280 | 1,653 |
| *Mycobacterium asiaticum* | 25276 | 2,023 |
| *Mycobacterium aurum* | 23366 | 2,042 |
| *Mycobacterium avium* | 25291 | 1,654 |
| *Mycobacterium austroafricanum* | 33464 | 2,298 |
| *Mycobacterium bovis* | 19210 | 1,986 |
| *Mycobacterium bovis* BCG | 35734 | 1,655 |
| *Mycobacterium celatum* | 51130 | 1,238 |
| *Mycobacterium chelonae* | 14472 | 2,141 |
| *Mycobacterium chitae* | 19627 | 1,557 |
| *Mycobacterium chubuense* | 27278 | 2,116 |
| *Mycobacterium dierhoferi* | 19340 | 1,996 |
| *Mycobacterium duvalii* | 43910 | 1,287 |
| *Mycobacterium engbaekii* | 27353 | 1,447 |
| *Mycobacterium farcinogenes* | 35753 | 1,728 |
| *Mycobacterium fallax* | 35219 | 2,536 |
| *Mycobacterium flavescens* | 14474 | 1,721 |
| *Mycobacterium fortuitum* | 6841 | 1,648 |
| *Mycobacterium fortuitum* ssp. acetamidolyticum | 35931 | 1,676 |
| *Mycobacterium gadium* | 27726 | 1,967 |
| *Mycobacterium gallinarum* | 19710 | 1,946 |
| *Mycobacterium gastri* | 15754 | 2,178 |
| *Mycobacterium gilvum* | 43909 | 1,244 |
| *Mycobacterium gordonae* | 14470 | 1,753 |
| *Mycobacterium haemophilum* .1 μg/rxn | 29854 | 1,227 |
| *Mycobacterium intracellulare* | 13950 | 1,776 |
| *Mycobacterium kansasii* | 12478 | 848,396 |
| *Mycobacterium komossense* | 33013 | 1,666 |
| *Mycobacterium lactis* | 27356 | 1,490 |
| *Mycobacterium malmoense* | 29571 | 1,940 |
| *Mycobacterium marinum* | 927 | 1,448 |
| *Mycobacterium microti* | 19422 | 1,277 |

TABLE 5-continued

Specificity of probes having nucleotide sequences SEQ ID NO: 7, SEQ ID NO: 8 and SEQ ID NO: 9 for *M. kansasii* over other mycobacteria.

| ORGANISM | ATCC # | RLU |
| --- | --- | --- |
| *Mycobacterium neoaurum* | 25795 | 1,135 |
| *Mycobacterium nonchromogenicum* | 19530 | 1,810 |
| *Mycobacterium obuense* | 27023 | 2,668 |
| *Mycobacterium parafortuitum* | 19686 | 2,244 |
| *Mycobacterium phlei* | 11758 | 1,563 |
| *Mycobacterium porcinum* | 33776 | 1,796 |
| *Mycobacterium poriferae* | 35087 | 1,856 |
| *Mycobacterium pulveris* | 35154 | 2,031 |
| *Mycobacterium rhodesiae* | 27024 | 1,996 |
| *Mycobacterium scrofulceum* | 19981 | 2,551 |
| *Mycobacterium shimoidei* | 27962 | 2,018 |
| *Mycobacterium simiae* | 25275 | 2,276 |
| *Mycobacterium smegmatis* | 14468 | 1,928 |
| *Mycobacterium sphagni* | 33027 | 2,233 |
| *Mycobacterium szulgai* | 35799 | 1,780 |
| *Mycobacterium terrae* | 15755 | 2,221 |
| *Mycobacterium thermoresistibile* | 19527 | 1,582 |
| *Mycobacterium tokaiense* | 27282 | 1,529 |
| *Mycobacterium triviale* | 23292 | 2,011 |
| *Mycobacterium tuberculosis* A | 25177 | 2,363 |
| *Mycobacterium tuberculosis* V | 27294 | 2,124 |
| *Mycobacterium vaccae* | 15483 | 1,959 |
| *Mycobacterium valentiae* | 29356 | 1,602 |
| *Mycobacterium xenopi* | 19250 | 1,775 |

EXAMPLE 7

In this experiment the specificity of the mix of probes and helpers used in Example 6 was tested against standard strains of bacteria. A total of 68 ATCC (American Type Culture Collection) reference strains were evaluated. These strains represented a phylogenetic cross section of organisms. Standard specificity testing was performed using growth obtained from actively growing cultures of the ATCC strains. Cell growth and lysis were as described in Example 2. Hybridization and detection were also as described in Example 2. All phylogenetic cross sectional organisms produced negative results well below the 30,000 RLU cut-off.

TABLE 6

Specificity of probes having nucleotide sequences SEQ ID NO: 7, SEQ ID NO: 8 and SEQ ID NO: 9 for *M. kansasii* over a phylogenetic cross section of organisms.

| ORGANISM | ATCC # | RLU |
| --- | --- | --- |
| *Acinetobacter calcoacelticus* | 33604 | 1,708 |
| *Actinomadura madurae* | 19425 | 1,602 |
| *Actinomyces pyogenes* | 19411 | 1,413 |
| *Actinoplanes italicus* | 27366 | 1,705 |
| *Aeromonas hydrophila* | 7966 | 2,707 |
| *Arthrobacter oxydans* | 14358 | 1,187 |
| *Bacillus subtilis* | 6051 | 6,682 |
| *Bordetella bronchiseptica* | 10580 | 1,796 |
| *Branhamella catarrhalis* | 25238 | 1,609 |
| *Brevibacterium linens* | 9172 | 3,057 |
| *Candida albicans* | 18804 | 1,363 |
| *Chromobacterium viotaceum* | 29094 | 2,153 |
| *Citrobacter freundii* | 8090 | 2,981 |
| *Corynebacterium aquaticum* | 14665 | 1,665 |
| *Corynebacterium diphtheriae* | 11913 | 2,027 |
| *Corynebacterium haemolyticum* | 9345 | 1,806 |
| *Corynebacterium matruchotii* | 33806 | 1,783 |
| *Corynebacterium minutissimum* | 23347 | 1,027 |
| *Corynebacterium pseudodiphtheriticum* | 10700 | 1,896 |

TABLE 6-continued

Specificity of probes having nucleotide sequences SEQ ID NO: 7, SEQ ID NO: 8 and SEQ ID NO: 9 for *M. kansasii* over a phylogenetic cross section of organisms.

| ORGANISM | ATCC # | RLU |
| --- | --- | --- |
| Cornyebacterium pseudogenitalium | 33035 | 1,767 |
| Corynebacterium pseudotuberculosis | 19410 | 2,408 |
| Corynebacterium renale | 19412 | 1,725 |
| Corynebacterium striatum | 6940 | 1,839 |
| Cryptococcus neoformans | 32045 | 1,921 |
| Deinococcus radiodurans | 35073 | 11,100 |
| Dermatophilus congolensis | 14637 | 1,420 |
| Enterobacter aerogenes | 13048 | 1,831 |
| Enterobacter cloacae | 13047 | 2,045 |
| Enterococcus faecalis | 19433 | 1,223 |
| Enterococcus faecium | 19434 | 1,406 |
| Escherichia coli | 10798 | 1,732 |
| Haemophilus influensae | 19418 | 3,099 |
| Haemophilus parainfluensae | 3392 | 1,856 |
| Klebsiella ozaenae | 11296 | 1,413 |
| Klebsiella pneumoniae | 23357 | 2,490 |
| Legionella micdadei | 33218 | 1,544 |
| Legionella pneumophilia | 33152 | 1,893 |
| Microbacterium lacticum | 8180 | 1,276 |
| Neisseria gonorrhoeae | 19424 | 2,502 |
| Neisseria meningitidis | 13077 | 3,593 |
| Nocardia brasiliensis | 19296 | 1,988 |
| Nocaraia farcinica | 3318 | 1,244 |
| Nocardia otitidis-caviarum | 14629 | 3,466 |
| Nocardiopsis dassonvillei | 23218 | 3,120 |
| Oerskovia turbata | 33225 | 1,136 |
| Oerskovia xanthineolytica | 27402 | 1,764 |
| Pseudomonas aeruginosa | 25330 | 2,080 |
| Rahnella aquatilis | 33071 | 1,767 |
| Rhodococcus aichiensis | 33611 | 1,689 |
| Rhodococcus bronchialis | 25592 | 3,095 |
| Rhodococcus chubuensis | 33609 | 1,146 |
| Rhodococcus equi | 6939 | 1,568 |
| Rhodococcus sputi | 29627 | 1,045 |
| Salmonella enteritidis | 13076 | 1,594 |
| Salmonella typhi | 6539 | 1,436 |
| Serratia marcescens | 13890 | 1,868 |
| Staphylococcus aureus | 12598 | 1,622 |
| Staphylococcus epidermis | 12228 | 1,600 |
| Streptococcus bovis | 33317 | 1,429 |
| Streptococcus equinus | 9812 | 1,964 |
| Streptococcus mitis | 9811 | 1,192 |
| Streptococcus pneumoniae | 6306 | 1,616 |
| Streptococcus pyogenes | 19615 | 1,618 |
| Streptococcus sp. Group C | 12388 | 1,821 |
| Streptomyces griseus | 23345 | 1,647 |
| Xanthomonas maltophilia | 13637 | 1,822 |
| Yersinia enterocolitica | 9610 | 1,456 |

EXAMPLE 8

The mix of hybridization probes (shown in Example 6) was tested for specificity to *M. kansasii* against 58 clinical isolates representing 7 species of mycobacteria Cell culture and growth, and hybridization, were as described in Example 2. No cross reactions were observed with closely related clinical isolates.

TABLE 7

Specificity of probe and helper mix for *M. kansasii* in clinical isolates.

| Organism | Site | RLU |
| --- | --- | --- |
| M. tuberculosis | CWVA | 1,171 |
| M. asiaticum | VAWH | 1,195 |
| M. asiaticum | VAWH | 1,278 |
| M. marinum | CWVA | 1,493 |

TABLE 7-continued

Specificity of probe and helper mix for *M. kansasii* in clinical isolates.

| Organism | Site | RLU |
| --- | --- | --- |
| M. avium | CWVA | 1,568 |
| M. marinum | CWVA | 1,583 |
| M. asiaticum | VAWH | 1,634 |
| M. tuberculosis | CWVA | 1,647 |
| M. avium | 628 | 1,698 |
| M. scrofulaceum | VAWH | 1,755 |
| M. avium | CWVA | 1,817 |
| M. gastri | NYC | 1,826 |
| M. scrofulaceum | VAWH | 1,755 |
| M. avium | CWVA | 1,817 |
| M. gastri | NYC | 1,826 |
| M. marinum | Mayo | 1,897 |
| M. avium | 631 | 1,960 |
| M. scrofulaceum | VAWH | 1,967 |
| M. gastri | NYC | 2,018 |
| M. scrofulaceum | VAWH | 2,034 |
| M. avium | 627 | 2,067 |
| M. gastri | NYC | 2,388 |
| M. gastri | NYC | 4,351 |
| M. marinum | CWVA | 20,046 |
| M. kansasii, atypical | Europe | 52,542 |
| M. kansasii | SKBL | 61,699 |
| M. kansasii | Mayo | 66,671 |
| M. kansasii | CWVA | 122,806 |
| M. kansasii | Mayo | 172,522 |
| M. kansasii, atypical | Europe | 232,362 |
| M. kansasii | CWVA | 306,988 |
| M. kansasii | Mayo | 336,892 |
| M. kansasii, atypical | Europe | 342,741 |
| M. kansasii | Mayo | 366,586 |
| M. kansasii, atypical | Europe | 406,881 |
| M. kansasii, atypical | Europe | 577,724 |
| M. kansasii, atypical | Europe | 588,268 |
| M. kansasii | CWVA | 611,845 |
| M. kansasii | CWVA | 653,662 |
| M. kansasii | CWVA | 691,591 |
| M. kansasii | CWVA | 713,305 |
| M. kansasii | VAWH | 789,324 |
| M. kansasii, atypical | Europe | 802,059 |
| M. kansasii | Mayo | 821,953 |
| M. kansasii, atypical | Europe | 827,164 |
| M. kansasii, atypical | Europe | 846,198 |
| M. kansasii | CWVA | 858,037 |
| M. kansasii, atypical | Europe | 905,348 |
| M. kansasii | CWVA | 911,333 |
| M. kansasii | CWVA | 931,887 |
| M. kansasii | CWVA | 948,911 |
| M. kansasii | CWVA | 954,200 |
| M. kansasii | ATCC | 964,110 |
| M. kansasii | CWVA | 1,013,473 |
| M. kansasii | CWVA | 1,020,477 |

EXAMPLE 9

In this experiment the sensitivity of the probe-helper mix (shown in Example 6) was tested with typical and atypical *M. kansasii* rRNA. The rRNA was used in concentrations of 0, 0.1, 0.25, 0.5 and 1 ng/µl. Testing was done in duplicate for each concentration and type of rRNA. 100 µl of rRNA from either the typical strain of *M. kansasii,* the BOV atypical strain, or the COU atypical strain was added to tubes containing lyophilized probe and hybridization reagents as described in Example 2. Reactions were vortexed and hybridized at 60° C. for 15 minutes. Detection was as described in Example 2.

The results show the probes are sensitive and capable of detecting low level amounts of *M. kansasii* typical and atypical rRN

TABLE 8

Sensitivity testing of probe and helper mix for typical and atypical rRNAs.

|  | RLU Rep 1 | RLU Rep 2 | Mean RLU | Net Mean RLU |
| --- | --- | --- | --- | --- |
| 0 ng typical rRNA |  |  |  | 710 |
| 10 ng typical rRNA | 22,467 | 20,954 | 21,711 | 21,001 |
| 25 ng typical rRNA | 40,802 | 43,360 | 42,081 | 41,371 |
| 50 ng typical rRNA | 86,300 | 92,517 | 89,409 | 88,699 |
| 100 ng typical rRNA | 181,211 | 165,301 | 173,256 | 172,546 |
| 0 ng BOV rRNA |  |  |  | 710 |
| 10 ng BOV rRNA | 31,871 | 30,823 | 31,347 | 30,637 |
| 25 ng BOV rRNA | 76,526 | 72,370 | 74,448 | 73,738 |
| 50 ng BOV rRNA | 136,198 | 135,937 | 136,068 | 135,358 |
| 100 ng BOV rRNA | 226,046 | 181,475 | 203,761 | 203,051 |
| 0 ng COU rRNA |  |  |  | 710 |
| 10 ng COU rRNA | 54,587 | 49,980 | 52,284 | 51,574 |
| 25 ng COU rRNA | 115,089 | 120,045 | 117,567 | 116,857 |
| 50 ng COU rRNA | 237,771 | 220,013 | 228,892 | 228,182 |
| 100 ng COU rRNA | 395,292 | 375,581 | 385,436 | 384,726 |

EXAMPLE 10

This experiment tested the sensitivity of the probe/helper mix of Example 6 for detecting *M. kansasii* rRNA in the presence of non-target cells with their rRNA and rDNA. Cells of *M. avium, M. gastri,* and *M. tuberculosis* were grown and lysed as described in Example 2. Samples were prepared with the appropriate mix of lysed non-target cells, and *M. kansasii* rRNA at a range from 0 ng to 100 ng, as indicated, and hybridization and detection were conducted as described in Example 2. The results show good signal recovery in the presence of a large number (around $1.5 \times 10^7$) of non-target cells.

TABLE 9

Sensitivity of probe/helper mix in the presence of nontarget cells.

|  | 100 ng rRNA | 50 ng rRNA | 25 ng rRNA | 10 ng rRNA | 1 ng rRNA | 0 ng rRNA |
| --- | --- | --- | --- | --- | --- | --- |
| *M. kansasii* rRNA alone | 187,549 | 109,790 | 55,499 | 21,888 | 3,018 | 794 |
| *M. kansasii* rRNA plus *M. avium* cells | 191,671 | 101,300 | 51,249 | 22,830 | 3,305 | 985 |
| percent recovery | 102 | 92 | 92 | 104 | 109 |  |
| *M. kansasii* rRNA plus *M. gastri* cells | 171,647 | 91,744 | 50,301 | 20,702 | 3,056 | 1,032 |
| percent recovery | 92 | 84 | 91 | 95 | 101 |  |
| *M. kansasii* rRNA plus *M. tuberculosis* cells | 199,513 | 102,465 | 50,466 | 21,196 | 2,267 | 1,607 |
| percent recovery | 106 | 93 | 91 | 97 | 75 |  |

The embodiments shown in the various examples described above confirm that the oligonucleotides herein described are capable of detecting *M. kansasii* nucleic acids, and can be used in an assay to distinguish *M. kansasii* from its known nearest phylogenetic neighbors. None of the examples described-herein are intended to limit the present invention to the embodiments of the preceding disclosure; additional embodiments are within the following claims.

We claim:

1. A hybridization assay probe for detecting the presence of *Mycobacterium kansasii* in a sample, said probe comprising an oligonucleotide up to 100 bases in length and having an at least 10 contiguous base region which is at least 80% complementary to an at least 10 contiguous base region present in a target sequence selected from the group consisting of: SEQ ID NO: 5, SEQ ID NO: 6, SEQ ID NO: 8, SEQ ID NO: 9, SEQ ID NO: 10, SEQ ID NO: 17, SEQ ID NO: 18, SEQ ID NO: 20, SEQ ID NO: 21 and SEQ ID NO: 22, wherein said probe forms a detectable duplex with nucleic acid from *Mycobacterium kansasii* under stringent hybridization conditions, and wherein said probe does not form a detectable duplex with nucleic acid from *Mycobacterium avium, Mycobacterium chelonae, Mycobacterium fortuitum, Mycobacterium gastri, Mycobacterium gordonae, Mycobacterium haemophilum, Mycobacterium intracellulare, Mycobacterium scrofulaceum, Mycobacterium simiae,* or *Mycobacterium tuberculosis* under said conditions.

2. The probe of claim 1, wherein the target sequence is SEQ ID NO: 5.

3. The probe of claim 1, wherein the target sequence is SEQ ID NO: 6.

4. The probe of claim 1, wherein the target sequence is SEQ ID NO: 8.

5. The probe of claim 1, wherein the target sequence is SEQ ID NO: 9.

6. The probe of claim 1, wherein the target sequence is SEQ ID NO: 10.

7. The probe of claim 1, wherein the target sequence is SEQ ID NO: 17.

8. The probe of claim 1, wherein the target sequence is SEQ ID NO: 18.

9. The probe of claim 1, wherein the target sequence is SEQ ID NO: 20.

10. The probe of claim 1, wherein the target sequence is SEQ ID NO: 21.

11. The probe of claim 1, wherein the target sequence is SEQ ID NO: 22.

12. The probe of claim 1, wherein said oligonucleotide is at least 80% complementary to the target sequence.

13. The probe of claim 1, wherein said oligonucleotide is at least 90% complementary to the target sequence.

14. The probe of claim 1, wherein said oligonucleotide is perfectly complementary to the target sequence.

15. The probe of claim 1, wherein said probe is at least 80% complementary to the target sequence.

16. The probe of claim 1, wherein said probe is at least 90% complementary to the target sequence.

17. The probe of claim 1, wherein said probe is perfectly complementary to the target sequence.

18. The probe of claim 17, wherein the target sequence is SEQ ID NO: 5.

19. The probe of claim 17, wherein the target sequence is SEQ ID NO: 6.

20. The probe of claim 17, wherein the target sequence is SEQ ID NO: 8.

21. The probe of claim 17, wherein the target sequence is SEQ ID NO: 9.

22. The probe of claim 17, wherein the target sequence is SEQ ID NO: 10.

23. The probe of claim 17, wherein the target sequence is SEQ ID NO: 17.

24. The probe of claim 17, wherein the target sequence is SEQ ID NO: 18.

25. The probe of claim 17, wherein the target sequence is SEQ ID NO: 20.

26. The probe of claim 17, wherein the target sequence is SEQ ID NO: 21.

27. The probe of claim 17, wherein the target sequence is SEQ ID NO: 22.

28. The probe of claim 1, wherein the target sequence is selected from the group consisting of: SEQ ID NO: 5, SEQ ID NO: 8, SEQ ID NO: 17 and SEQ ID NO: 20.

29. The probe of claim 28, wherein said *Mycobacterium kansasii* is the *Mycobacterium kansasii* BOV subspecies.

30. The probe of claim 1, wherein the target sequence is selected from the group consisting of: SEQ ID NO: 6, SEQ ID NO: 9, SEQ ID NO: 10, SEQ ID NO: 18, SEQ ID NO: 21 and SEQ ID NO: 22.

31. The probe of claim 30, wherein said *Mycobacterium kansasii* is the *Mycobactetium kansasii* COU subspecies.

32. The probe of claim 1, wherein said probe includes a label.

33. The probe of claim 32, wherein said label is an acridinium ester.

34. A detectable duplex formed between the probe of claim 1 and nucleic acid from *Mycobacterium kansasii*.

35. A probe mix for detecting the presence of *Mycobacterium kansasii* in a sample, said probe mix comprising:
  a) a hybridization assay probe comprising an oligonucleotide up to 100 bases in length and having an at least 10 contiguous base region which is at least 80% homologous to an at least 10 contiguous base region present in a first sequence selected from the group consisting of: SEQ ID NO: 5, SEQ ID NO: 6, SEQ ID NO: 8, SEQ ID NO: 9, SEQ ID NO: 10, SEQ ID NO: 17, SEQ ID NO: 18, SEQ ID NO: 20, SEQ ID NO: 21 and SEQ ID NO: 22; and
  b) a helper probe comprising an oligonucleotide up to 100 bases in length and having an at least 10 contiguous base region which is at least 80% homologous to an at least 10 contiguous base region present in a second sequence selected from the group consisting of: SEQ ID NO: 11, SEQ ID NO: 12, SEQ ID NO: 15, SEQ ID NO: 23, SEQ ID NO: 24, SEQ ID NO: 25, SEQ ID NO: 26 and SEQ ID NO: 27,
  wherein said hybridization assay probe forms a detectable duplex with nucleic acid from *Mycobacterium kansasii* under stringent hybridization conditions, and
  wherein said hybridization assay probe does not form a detectable duplex with nucleic acid from *Mycobacterium avium, Mycobacterium chelonae, Mycobacterium fortuitum, Mycobactenium gastri, Mycobacterium gordonae, Mycobacterium haemophilum, Mycobacterium intracellulare, Mycobacterium scrofulacelum, Mycobacterium simiae,* or *Mycobacterium tuberculosis* under said conditions.

36. The probe mix of claim 35, wherein the first sequence is selected from the group consisting of: SEQ ID NO: 5, SEQ ID NO: 8, SEQ ID NO: 17 and SEQ ID NO: 20.

37. The probe mix of claim 36, wherein the oligonucleotide of said hybridization assay probe shares at least 90% base homology with the first target sequence.

38. The probe mix of claim 36, wherein the oligonucleotide of said hybridization assay probe has the base sequence of SEQ ID NO: 8.

39. The probe mix of claim 36, wherein said probe has the base sequence of SEQ ID NO: 8.

40. The probe mix of claim 35, wherein the first sequence is selected from the group consisting of: SEQ ID NO: 6, SEQ ID NO: 9, SEQ ID NO: 10, SEQ ID NO: 18, SEQ ID NO: 21 and SEQ ID NO: 22.

41. The probe mix of claim 40, wherein the oligonucleotide of said hybridization assay probe shares at least 90% base homology with the first sequence.

42. The probe mix of claim 40, wherein the oligonucleotide of said hybridization assay probe has the base sequence of SEQ ID NO: 9.

43. The probe mix of claim 40, wherein said probe has the base sequence of SEQ ID NO: 9.

44. The probe mix of claim 36 or 40, wherein the second sequence is selected from the group consisting of: SEQ ID NO: 15, SEQ ID NO: 25, SEQ ID NO: 26 and SEQ ID NO: 27.

45. The probe mix of claim 37 or 41, wherein the oligonucleotide of said helper probe shares at least 90% base homology with SEQ ID NO: 15.

46. The probe mix of claim 38 or 42 wherein said helper probe has the base sequence of SEQ ID NO: 15.

47. The probe mix of claim 35, wherein said probe includes a label.

48. The probe mix of claim 47, wherein said label is an acridinium ester.

49. A probe mix for detecting the presence of *Mycobacterium kansasii* in a sample, said probe mix comprising:
  a) a first hybridization assay probe comprising a first oligonucleotide up to 100 bases in length and having an at least 10 contiguous base region which is at least 80% homologous to an at least 10 contiguous base region present in a first sequence selected from the group consisting of: SEQ ID NO: 5, SEQ ID NO: 8, SEQ ID NO: 17 and SEQ ID NO: 20; and
  b) a second hybridization assay probe comprising a second oligonucleotide up to 100 bases in length and having an at least 10 contiguous base region which is at least 80% homologous to an at least 10 contiguous base region present in a second target sequence selected from the group consisting of: SEQ ID NO: 6, SEQ ID NO: 9, SEQ ID NO: 10, SEQ ID NO: 18, SEQ ID NO: 21 and SEQ ID NO: 22,
  wherein each of said probes forms a detectable duplex with nucleic acid from *Mycobacterium kansasii* under stringent hybridization conditions, and
  wherein each of said probes does not form a detectable duplex with nucleic acid from *Mycobacterium avium, Mycobacterium chelonae, Mycobacterium-fortuitum, Mycobacterium gastri, Mycobacterium gordonae, Mycobacterium haemophilum, Mycobacterium intracellulare, Mycobacterium scrofulacelum, Mycobacterium simiae,* or *Mycobacterium tuberculosis* under said conditions.

50. The probe mix of claim 49 further comprising a helper probe containing an oligonucleotide up to 100 bases in length and having an at least 10 contiguous base region which is at least 80% homologous to an at least 10 contiguous base region present in a third sequence selected from the group consisting of: SEQ ID NO: 11, SEQ ID NO: 12, SEQ ID NO: 13, SEQ ID NO: 14, SEQ ID NO: 15, SEQ ID NO: 23, SEQ ID NO: 24, SEQ ID NO: 25, SEQ ID NO: 26 and SEQ ID NO: 27.

51. The probe mix of claim 49 further comprising a helper probe containing an oligonucleotide up to 100 bases in length and having an at least 10 contiguous base region which is at least 80% homologous to an at least 10 contiguous base region present in a third sequence selected from the group consisting of: SEQ ID NO: 13, SEQ ID NO: 14, SEQ ID NO: 15, SEQ ID NO: 25, SEQ ID NO: 26 and SEQ ID NO: 27.

52. The probe mix of claim 49, wherein the first sequence is SEQ ID NO: 8 and the second sequence is SEQ ID NO: 9.

53. The probe mix of claim 52, wherein the oligonucleotide of said first probe shares at least 90% base homology with SEQ ID NO: 8 and the oligonucleotide of said second probe shares at least 90% base homology with SEQ ID NO: 9.

54. The probe mix of claim 52, wherein said first probe has the base sequence of SEQ ID NO: 8 and said second probe has the base sequence of SEQ ID NO: 9.

55. The probe mix of claim 53, 53 or 54 further comprising a helper probe containing an oligonucleotide up to 100 bases in length and having an at least 10 contiguous base region which is at least 80% homologous to an at least 10 contiguous base region present in a third sequence selected from the group consisting of: SEQ ID NO: 13, SEQ ID NO: 14 and SEQ ID NO: 15.

56. The probe mix of claim 55, wherein the oligonucleotide of said helper probe shares at least 90% base homology with the third sequence.

57. The probe mix of claim 55, wherein said helper probe has the base sequence of the third sequence.

58. The probe mix of claim 49, wherein at least one of said probes includes a label.

59. The probe mix of claim 58, wherein said label is an acridinium ester.

60. A probe mix for detecting the presence of *Mycobacterium kansasii* in a sample, said probe mix comprising:
   a) a first hybridization assay probe comprising a first oligonucleotide up to 100 bases in length and having an at least 10 contiguous base region which is at least 80% homologous to an at least 10 contiguous base region present in a first sequence selected from the group consisting of: SEQ ID NO: 4, SEQ ID NO: 7, SEQ ID NO: 16 and SEQ ID NO: 19;
   b) a second hybridization assay probe comprising a second oligonucleotide up to 100 bases in length and having an at least 10 contiguous base region which is at least 80% homologous to an at least 10 contiguous base region present in a second sequence selected from the group consisting of: SEQ ID NO: 5, SEQ ID NO: 8, SEQ ID NO: 17 and SEQ ID NO: 20; and
   c) a third hybridization assay probe comprising a third oligonucleotide up to 100 bases in length and having an at least 10 contiguous base region which is at least 80% homologous to an at least 10 contiguous base region present in a third sequence selected from the group consisting of: SEQ ID NO: 6, SEQ ID NO: 9, SEQ ID NO: 10, SEQ ID NO: 18, SEQ ID NO: 21 and SEQ ID NO: 22,
   wherein each of said probes forms a detectable duplex with nucleic acid from *Mycobacterium kansasii* under stringent hybridization conditions, and
   wherein each of said probes does not form a detectable duplex with nucleic acid from *Mycobacterium avium, Mycobacterium chelonae, Mycobacterium-fortuitum, Mycobacterium gastri, Mycobacterium gordonae, Mycobacterium haemophilum, Mycobacterium intracellulare, Mycobacterium scro lacelum, Mycobacterium simiae,* or *Mycobacterium tuberculosis* under said conditions.

61. The probe mix of claim 60 further comprising a helper probe containing an oligonucleotide up to 100 bases in length and having an at least 10 contiguous base region which is at least 80% homologous to an at least 10 contiguous base region present in a fourth sequence selected from the group consisting of: SEQ ID NO: 11, SEQ ID NO: 12, SEQ ID NO: 13, SEQ ID NO: 14, SEQ ID NO: 15, SEQ ID NO: 23, SEQ ID NO: 24, SEQ ID NO: 25, SEQ ID NO: 26 and SEQ ID NO: 27.

62. The probe mix of claim 60 further comprising a helper probe containing an oligonucleotide up to 100 bases in length and having an at least 10 contiguous base region which is at least 80% homologous to an at least 10 contiguous base region present in a fourth sequence selected from the group consisting of: SEQ ID NO: 13, SEQ ID NO: 14, SEQ ID NO: 15, SEQ ID NO: 25, SEQ ID NO: 26 and SEQ ID NO: 27.

63. The probe mix of claim 60, wherein said first sequence is SEQ ID NO: 7, said second sequence is SEQ ID NO: 8, and said third sequence is SEQ ID NO: 9.

64. The probe mix of claim 63, wherein the oligonucleotide of said first probe shares at least 90% base homology with the sequence of SEQ ID NO: 7, the oligonucleotide of said second probe shares at least 90% base homology with the sequence of SEQ ID NO: 8, and the oligonucleotide of said third probe shares at least 90% base homology with the sequence of SEQ ID NO: 9.

65. The probe mix of claim 64, wherein said first probe has the base sequence of SEQ ID NO: 7, said second probe has the base sequence of SEQ ID NO: 8, and said third probe has the base sequence of SEQ ID NO: 9.

66. The probe mix of claim 63 further comprising a helper probe containing an oligonucleotide up to 100 bases in length and having an at least 10 contiguous base region which is at least 80% homologous to an at least 10 contiguous base region present in a fourth sequence selected from the group consisting of: SEQ ID NO: 13, SEQ ID NO: 14 and SEQ ID NO: 15.

67. The probe mix of claim 64 further comprising first and second helper probes, wherein said first helper probe shares at least 90% base homology with SEQ ID NO: 13 and said second helper probe shares at least 90% base homology with SEQ ID NO: 14.

68. The probe mix of claim 65 further comprising first and second helper probes, wherein said first helper probe has the base sequence of SEQ ID NO: 13 and said second helper probe has the base sequence of SEQ ID NO: 14.

69. A method for detecting the presence of *Mycobacterium kansasii* in a sample, said method comprising the steps of:
   a) providing to said sample the probe of any one of claims 1–33;
   b) incubating said sample under conditions such that said probe hybridizes to *Mycobacterium kansasii* nucleic acid, thereby forming a detectable duplex,
   wherein said probe does not form a detectable duplex with nucleic acid from *Mycobacterium avium, Mycobacterium chelonae, Mycobacterium fortuitum, Mycobacterium gastri, Mycobacterium gordonae, Mycobacterium haemophilum, Mycobacterium intracellulare, Mycobacterium scrofulacelum, Mycobacterium simiae,* or *Mycobacterium tuberculosis* under said conditions; and
   c) detecting the duplex of step b) as an indication of the presence of *Mycobacterium kansasii* in said sample.

\* \* \* \* \*

SEQUENCE LISTING (1) GENERAL INFORMATION:

(iii) NUMBER OF SEQUENCES:    33

(2) INFORMATION FOR SEQ ID NO: 1:

(i) SEQUENCE CHARACTERISTICS:
       (A) LENGTH:         76 base pairs
       (B) TYPE:           nucleic acid
       (C) STRANDEDNESS:   single
       (D) TOPOLOGY:       linear (ii) MOLECULE TYPE:     RNA (genomic)

(xi) SEQUENCE DESCRIPTION: SEQ ID NO: 1:

GCCGCAGCGA AAGCGAGUCU GAAUAGGGCG UAUCGCGCGC GAGCGUGUGU AGUGGCGUGU       60

UCUGGACCCG AAGCGG                                                      76

(2) INFORMATION FOR SEQ ID NO: 2:

(i) SEQUENCE CHARACTERISTICS:
       (A) LENGTH:         76 base pairs
       (B) TYPE:           nucleic acid
       (C) STRANDEDNESS:   single
       (D) TOPOLOGY:       linear (ii) MOLECULE TYPE:     RNA (genomic)

(xi) SEQUENCE DESCRIPTION: SEQ ID NO: 2:

GCCGCAGCGA AAGCGAGUCU GAAUAGGGCG UAUCACGCGU GAGCGUGUGU AGUGGCGUGU       60

UCUGGACCCG AAGCGG                                                      76

(2) INFORMATION FOR SEQ ID NO: 3:

(i) SEQUENCE CHARACTERISTICS:
       (A) LENGTH:         76 base pairs
       (B) TYPE:           nucleic acid
       (C) STRANDEDNESS:   single
       (D) TOPOLOGY:       linear (ii) MOLECULE TYPE:     RNA (genomic)

(xi) SEQUENCE DESCRIPTION: SEQ ID NO: 3:

GCCGCAGCGA AAGCGAGUCU GAAUAGGGCG UAUCACGUGC AAGCGUGUGU AGUGGCGUGU       60

UCUGGACCCG AAGCGG                                                      76

(2) INFORMATION FOR SEQ ID NO: 4:

(i) SEQUENCE CHARACTERISTICS:
       (A) LENGTH:         18 base pairs
       (B) TYPE:           nucleic acid
       (C) STRANDEDNESS:   single
       (D) TOPOLOGY:       linear (ii) MOLECULE TYPE:     RNA (genomic)

(xi) SEQUENCE DESCRIPTION: SEQ ID NO: 4:

GCGUAUCGCG CGCGAGCG                                                    18

(2) INFORMATION FOR SEQ ID NO: 5:

(i) SEQUENCE CHARACTERISTICS:
       (A) LENGTH:         19 base pairs
       (B) TYPE:           nucleic acid

```
        (C) STRANDEDNESS:    single
        (D) TOPOLOGY:        linear (ii) MOLECULE TYPE:      RNA (genomic)

(xi) SEQUENCE DESCRIPTION: SEQ ID NO: 5:

GGCGUAUCAC GCGUGAGCG                                                    19

(2) INFORMATION FOR SEQ ID NO: 6:

(i) SEQUENCE CHARACTERISTICS:
        (A) LENGTH:          19 base pairs
        (B) TYPE:            nucleic acid
        (C) STRANDEDNESS:    single
        (D) TOPOLOGY:        linear (ii) MOLECULE TYPE:      RNA (genomic)

(xi) SEQUENCE DESCRIPTION: SEQ ID NO: 6:

GGCGUAUCAC GUGCAAGCG                                                    19

(2) INFORMATION FOR SEQ ID NO: 7:

(i) SEQUENCE CHARACTERISTICS:
        (A) LENGTH:          18 base pairs
        (B) TYPE:            nucleic acid
        (C) STRANDEDNESS:    single
        (D) TOPOLOGY:        linear (ii) MOLECULE TYPE:      DNA (genomic)

(xi) SEQUENCE DESCRIPTION: SEQ ID NO: 7:

CGCTCGCGCG CGATACGC                                                     18

(2) INFORMATION FOR SEQ ID NO: 8:

(i) SEQUENCE CHARACTERISTICS:
        (A) LENGTH:          19 base pairs
        (B) TYPE:            nucleic acid
        (C) STRANDEDNESS:    single
        (D) TOPOLOGY:        linear (ii) MOLECULE TYPE:      DNA (genomic)

(xi) SEQUENCE DESCRIPTION: SEQ ID NO: 8:

CGCTCACGCG TGATACGCC                                                    19

(2) INFORMATION FOR SEQ ID NO: 9:

(i) SEQUENCE CHARACTERISTICS:
        (A) LENGTH:          18 base pairs
        (B) TYPE:            nucleic acid
        (C) STRANDEDNESS:    single
        (D) TOPOLOGY:        linear (ii) MOLECULE TYPE:      DNA (genomic)

(xi) SEQUENCE DESCRIPTION: SEQ ID NO: 9:

CGCTTGCACG TGATACGC                                                     18

(2) INFORMATION FOR SEQ ID NO: 10:

(i) SEQUENCE CHARACTERISTICS:
        (A) LENGTH:          19 base pairs
        (B) TYPE:            nucleic acid
        (C) STRANDEDNESS:    single
        (D) TOPOLOGY:        linear (ii) MOLECULE TYPE:      DNA (genomic)
```

(xi) SEQUENCE DESCRIPTION: SEQ ID NO: 10:

CGCTTGCACG TGATACGCC                                                    19

(2) INFORMATION FOR SEQ ID NO: 11:

(i) SEQUENCE CHARACTERISTICS:
        (A) LENGTH:          27 base pairs
        (B) TYPE:            nucleic acid
        (C) STRANDEDNESS:    single
        (D) TOPOLOGY:        linear (ii) MOLECULE TYPE:      RNA (genomic)

(xi) SEQUENCE DESCRIPTION: SEQ ID NO: 11:

GCCGCAGCGA AGCGAGUCU GAAUAGG                                            27

(2) INFORMATION FOR SEQ ID NO: 12:

(i) SEQUENCE CHARACTERISTICS:
        (A) LENGTH:          31 base pairs
        (B) TYPE:            nucleic acid
        (C) STRANDEDNESS:    single
        (D) TOPOLOGY:        linear (ii) MOLECULE TYPE:      RNA (genomic)

(xi) SEQUENCE DESCRIPTION: SEQ ID NO: 12:

UGUGUAGUGG CGUGUUCUGG ACCCGAAGCG G                                      31

(2) INFORMATION FOR SEQ ID NO: 13:

(i) SEQUENCE CHARACTERISTICS:
        (A) LENGTH:          27 base pairs
        (B) TYPE:            nucleic acid
        (C) STRANDEDNESS:    single
        (D) TOPOLOGY:        linear (ii) MOLECULE TYPE:      DNA (genomic)

(xi) SEQUENCE DESCRIPTION: SEQ ID NO: 13:

CGTATTCAGA CTCGCTTTCG CTGCGGC                                           27

(2) INFORMATION FOR SEQ ID NO: 14:

(i) SEQUENCE CHARACTERISTICS:
        (A) LENGTH:          31 base pairs
        (B) TYPE:            nucleic acid
        (C) STRANDEDNESS:    single
        (D) TOPOLOGY:        linear (ii) MOLECULE TYPE:      DNA (genomic)

(xi) SEQUENCE DESCRIPTION: SEQ ID NO: 14:

CCGCTTCGGG TCCAGAACAC GCCACTACAC A                                      31

(2) INFORMATION FOR SEQ ID NO: 15:

(i) SEQUENCE CHARACTERISTICS:
        (A) LENGTH:          26 base pairs
        (B) TYPE:            nucleic acid
        (C) STRANDEDNESS:    single
        (D) TOPOLOGY:        linear (ii) MOLECULE TYPE:      DNA (genomic)

(xi) SEQUENCE DESCRIPTION: SEQ ID NO: 15:

CTATTCAGAC TCGCTTTCGC TGCGGC                                            26

(2) INFORMATION FOR SEQ ID NO: 16:

(i) SEQUENCE CHARACTERISTICS:
        (A) LENGTH:          18 base pairs
        (B) TYPE:            nucleic acid
        (C) STRANDEDNESS:    single
        (D) TOPOLOGY:        linear (ii) MOLECULE TYPE:      DNA (genomic)

(xi) SEQUENCE DESCRIPTION: SEQ ID NO: 16:

GCGTATCGCG CGCGAGCG                                                          18

(2) INFORMATION FOR SEQ ID NO: 17:

(i) SEQUENCE CHARACTERISTICS:
        (A) LENGTH:          19 base pairs
        (B) TYPE:            nucleic acid
        (C) STRANDEDNESS:    single
        (D) TOPOLOGY:        linear (ii) MOLECULE TYPE:      DNA (genomic)

(xi) SEQUENCE DESCRIPTION: SEQ ID NO: 17:

GGCGTATCAC GCGTGAGCG                                                         19

(2) INFORMATION FOR SEQ ID NO: 18:

(i) SEQUENCE CHARACTERISTICS:
        (A) LENGTH:          19 base pairs
        (B) TYPE:            nucleic acid
        (C) STRANDEDNESS:    single
        (D) TOPOLOGY:        linear (ii) MOLECULE TYPE:      DNA (genomic)

(xi) SEQUENCE DESCRIPTION: SEQ ID NO: 18:

GGCGTATCAC GTGCAAGCG                                                         19

(2) INFORMATION FOR SEQ ID NO: 19:

(i) SEQUENCE CHARACTERISTICS:
        (A) LENGTH:          18 base pairs
        (B) TYPE:            nucleic acid
        (C) STRANDEDNESS:    single
        (D) TOPOLOGY:        linear (ii) MOLECULE TYPE:      RNA (genomic)

(xi) SEQUENCE DESCRIPTION: SEQ ID NO: 19:

CGCUCGCGCG CGAUACGC                                                          18

(2) INFORMATION FOR SEQ ID NO: 20:

(i) SEQUENCE CHARACTERISTICS:
        (A) LENGTH:          19 base pairs
        (B) TYPE:            nucleic acid
        (C) STRANDEDNESS:    single
        (D) TOPOLOGY:        linear (ii) MOLECULE TYPE:      RNA (genomic)

(xi) SEQUENCE DESCRIPTION: SEQ ID NO: 20:

CGCUCACGCG UGAUACGCC                                                         19

(2) INFORMATION FOR SEQ ID NO: 21:

```
    (i) SEQUENCE CHARACTERISTICS:
        (A) LENGTH:          18 base pairs
        (B) TYPE:            nucleic acid
        (C) STRANDEDNESS:    single
        (D) TOPOLOGY:        linear (ii) MOLECULE TYPE:      RNA (genomic)

(xi) SEQUENCE DESCRIPTION: SEQ ID NO: 21:

CGCUUGCACG UGAUACGC                                                      18

(2) INFORMATION FOR SEQ ID NO: 22:

(i) SEQUENCE CHARACTERISTICS:
        (A) LENGTH:          19 base pairs
        (B) TYPE:            nucleic acid
        (C) STRANDEDNESS:    single
        (D) TOPOLOGY:        linear (ii) MOLECULE TYPE:      RNA (genomic)

(xi) SEQUENCE DESCRIPTION: SEQ ID NO: 22:

CGCUUGCACG UGAUACGCC                                                     19

(2) INFORMATION FOR SEQ ID NO: 23:

(i) SEQUENCE CHARACTERISTICS:
        (A) LENGTH:          27 base pairs
        (B) TYPE:            nucleic acid
        (C) STRANDEDNESS:    single
        (D) TOPOLOGY:        linear (ii) MOLECULE TYPE:      DNA (genomic)

(xi) SEQUENCE DESCRIPTION: SEQ ID NO: 23:

GCCGCAGCGA AAGCGAGTCT GAATAGG                                            27

(2) INFORMATION FOR SEQ ID NO: 24:

(i) SEQUENCE CHARACTERISTICS:
        (A) LENGTH:          31 base pairs
        (B) TYPE:            nucleic acid
        (C) STRANDEDNESS:    single
        (D) TOPOLOGY:        linear (ii) MOLECULE TYPE:      DNA (genomic)

(xi) SEQUENCE DESCRIPTION: SEQ ID NO: 24:

TGTGTAGTGG CGTGTTCTGG ACCCGAAGCG G                                       31

(2) INFORMATION FOR SEQ ID NO: 25:

(i) SEQUENCE CHARACTERISTICS:
        (A) LENGTH:          27 base pairs
        (B) TYPE:            nucleic acid
        (C) STRANDEDNESS:    single
        (D) TOPOLOGY:        linear (ii) MOLECULE TYPE:      RNA (genomic)

(xi) SEQUENCE DESCRIPTION: SEQ ID NO: 25:

CGUAUUCAGA CUCGCUUUCG CUGCGGC                                            27

(2) INFORMATION FOR SEQ ID NO: 26:

(i) SEQUENCE CHARACTERISTICS:
        (A) LENGTH:          31 base pairs
        (B) TYPE:            nucleic acid
        (C) STRANDEDNESS:    single
```

```
          (D) TOPOLOGY:       linear (ii) MOLECULE TYPE:     RNA (genomic)

(xi) SEQUENCE DESCRIPTION: SEQ ID NO: 26:

CCGCUUCGGG UCCAGAACAC GCCACUACAC A                              31

(2) INFORMATION FOR SEQ ID NO: 27:

(i) SEQUENCE CHARACTERISTICS:
          (A) LENGTH:         26 base pairs
          (B) TYPE:           nucleic acid
          (C) STRANDEDNESS:   single
          (D) TOPOLOGY:       linear (ii) MOLECULE TYPE:     RNA (genomic)

(xi) SEQUENCE DESCRIPTION: SEQ ID NO: 27:

CUAUUCAGAC UCGCUUUCGC UGCGGC                                    26

(2) INFORMATION FOR SEQ ID NO: 28:

(i) SEQUENCE CHARACTERISTICS:
          (A) LENGTH:         7 base pairs
          (B) TYPE:           nucleic acid
          (C) STRANDEDNESS:   single
          (D) TOPOLOGY:       linear (ii) MOLECULE TYPE:     RNA (genomic)

(xi) SEQUENCE DESCRIPTION: SEQ ID NO: 28:

GCGCGCG                                                          7

(2) INFORMATION FOR SEQ ID NO: 29:

(i) SEQUENCE CHARACTERISTICS:
          (A) LENGTH:         7 base pairs
          (B) TYPE:           nucleic acid
          (C) STRANDEDNESS:   single
          (D) TOPOLOGY:       linear (ii) MOLECULE TYPE:     RNA (genomic)

(xi) SEQUENCE DESCRIPTION: SEQ ID NO: 29:

ACGCGUG                                                          7

(2) INFORMATION FOR SEQ ID NO: 30:

(i) SEQUENCE CHARACTERISTICS:
          (A) LENGTH:         7 base pairs
          (B) TYPE:           nucleic acid
          (C) STRANDEDNESS:   single
          (D) TOPOLOGY:       linear (ii) MOLECULE TYPE:     RNA (genomic)

(xi) SEQUENCE DESCRIPTION: SEQ ID NO: 30:

ACGUGCG                                                          7

(2) INFORMATION FOR SEQ ID NO: 31:

(i) SEQUENCE CHARACTERISTICS:
          (A) LENGTH:         7 base pairs
          (B) TYPE:           nucleic acid
          (C) STRANDEDNESS:   single
          (D) TOPOLOGY:       linear (ii) MOLECULE TYPE:     RNA (genomic)
```

(xi) SEQUENCE DESCRIPTION: SEQ ID NO: 31:

CGCGCGC                                                                              7

(2) INFORMATION FOR SEQ ID NO: 32:

(i) SEQUENCE CHARACTERISTICS:
        (A) LENGTH:           7 base pairs
        (B) TYPE:             nucleic acid
        (C) STRANDEDNESS:     single
        (D) TOPOLOGY:         linear (ii) MOLECULE TYPE:       RNA (genomic)

(xi) SEQUENCE DESCRIPTION: SEQ ID NO: 32:

CACGCGU                                                                              7

(2) INFORMATION FOR SEQ ID NO: 33:

(i) SEQUENCE CHARACTERISTICS:
        (A) LENGTH:           7 base pairs
        (B) TYPE:             nucleic acid
        (C) STRANDEDNESS:     single
        (D) TOPOLOGY:         linear (ii) MOLECULE TYPE:       RNA (genomic)

(xi) SEQUENCE DESCRIPTION: SEQ ID NO: 33:

CGCACGU                                                                              7